(12) United States Patent
Kim et al.

(10) Patent No.: US 11,013,670 B2
(45) Date of Patent: May 25, 2021

(54) HYALURONIC ACID MICROSTRUCTURE HAVING EXCELLENT SOLUBILITY CHARACTERISTICS

(71) Applicant: ENDODERMA CO., LTD., Chungcheongbuk-do (KR)

(72) Inventors: Jae Soo Kim, Gyeonggi-do (KR); Soon Chang Kwon, Daejeon (KR); Sang Jin Park, Gyeonggi-do (KR)

(73) Assignee: ENDODERMA CO., LTD., Chungcheongbuk-do (KR)

(*) Notice: Subject to any disclaimer, the term of this patent is extended or adjusted under 35 U.S.C. 154(b) by 21 days.

(21) Appl. No.: 16/310,488

(22) PCT Filed: Jun. 16, 2017

(86) PCT No.: PCT/KR2017/006342
§ 371 (c)(1),
(2) Date: Dec. 17, 2018

(87) PCT Pub. No.: WO2017/217818
PCT Pub. Date: Dec. 21, 2017

(65) Prior Publication Data
US 2019/0336411 A1    Nov. 7, 2019

(30) Foreign Application Priority Data

Jun. 16, 2016 (KR) .......................... 10-2016-0074985

(51) Int. Cl.
*A61K 8/02* (2006.01)
*A61K 8/73* (2006.01)
*A61Q 19/08* (2006.01)

(52) U.S. Cl.
CPC ............ *A61K 8/0216* (2013.01); *A61K 8/735* (2013.01); *A61Q 19/08* (2013.01); *A61K 2800/91* (2013.01)

(58) Field of Classification Search
CPC ..... A61K 8/0216; A61K 8/735; A61K 9/0021
See application file for complete search history.

(56) References Cited

U.S. PATENT DOCUMENTS

| | | | | |
|---|---|---|---|---|
| 10,493,160 B2* | 12/2019 | Kim | ................. | B29C 45/40 |
| 2004/0197311 A1* | 10/2004 | Brekke | ................. | A61K 35/28 |
| | | | | 424/93.7 |
| 2010/0316683 A1 | 12/2010 | Piron et al. | | |
| 2011/0195124 A1 | 8/2011 | Jin | | |
| 2013/0203856 A1* | 8/2013 | Cho | ................. | C08B 37/0072 |
| | | | | 514/626 |
| 2014/0180201 A1* | 6/2014 | Ding | ................. | A61M 37/0015 |
| | | | | 604/46 |
| 2014/0200508 A1 | 7/2014 | Cohen et al. | | |
| 2015/0209563 A1 | 7/2015 | Amir | | |
| 2017/0304602 A1 | 10/2017 | Liu et al. | | |
| 2018/0021437 A1 | 1/2018 | Kim et al. | | |
| 2019/0001109 A1 | 1/2019 | Kim et al. | | |

FOREIGN PATENT DOCUMENTS

| | | | |
|---|---|---|---|
| CN | 104921961 A | 9/2015 | |
| EP | 3 257 549 A1 | 12/2017 | |
| EP | 3 398 645 A1 | 11/2018 | |
| JP | H08157378 A | 6/1996 | |
| JP | 2005272398 A | 10/2005 | |
| JP | 2009-201956 A | 9/2009 | |
| JP | 2012-505164 A | 3/2012 | |
| JP | 5267910 B2 | 8/2013 | |
| JP | 2015522342 A | 8/2015 | |
| JP | 2016093325 A | 5/2016 | |
| KR | 10-2014-0051648 A | 5/2014 | |
| KR | 20140101018 * | 8/2014 | .............. A61F 2/00 |
| KR | 10-2016-0100265 A | 8/2016 | |
| TW | 200836778 A | 9/2008 | |
| WO | WO-2010/040271 A1 | 4/2010 | |
| WO | WO-2014/041531 A1 | 3/2014 | |
| WO | WO-2016-076442 A1 | 5/2016 | |
| WO | WO-2016129967 A1 | 8/2016 | |

OTHER PUBLICATIONS

Office Action from corresponding Japanese Patent Application No. 2018-565661, dated Oct. 1, 2019.

(Continued)

*Primary Examiner* — Pancham Bakshi

(74) *Attorney, Agent, or Firm* — Harness, Dickey & Pierce, P.L.C.

(57) ABSTRACT

The present invention relates to a hyaluronic acid microstructure having excellent solubility characteristics. More specifically, the present invention relates to a biodegradable microstructure comprising crosslinked hyaluronic acid and having excellent solubility characteristics during skin penetration. When the microstructure of the present invention is penetrated into the skin, the solubility characteristics in the skin are excellent, the dissolution rate in the skin can be easily controlled according to the content ratio of the crosslinked hyaluronic acid, and, while effective ingredients provided on the microstructure can be stably delivered into the skin, the release rate of the provided effective ingredients can be easily controlled, and thus the present invention can be used as a transdermal delivery system for pharmacologically active materials or skin improvement materials.

15 Claims, 17 Drawing Sheets

(56) References Cited

OTHER PUBLICATIONS

Extended European Search Report from corresponding European Patent Application No. 17813641.2, dated May 17, 2019.
Park, Y., et al.; "Fabrication and characterization of dissolving microneedle arrays for improving skin permeability of cosmetic ingredients". Journal of Industrial and Engineering Chemistry, The Korean Society of Industrial and Engineering Chemistry, Korea, vol. 39, May 30, 2016 (May 30, 2016), pp. 121-126,XP029631024, ISSN: 1226-086X, DOI: 10.1016/J.JIEC.2016.05.022, * "fabrication of SH microneedle array"; p. 123 * * p. 124, right-hand column, paragraph 2-p. 125, left-hand column, paragraph 2 *.
Office Action from corresponding Korean Patent Application No. 10-2017-0076877, dated Aug. 14, 2018.
Office Action from corresponding Taiwanese Patent Application No. 106120234, dated Apr. 19, 2018.
International Search Report from corresponding PCT Application No. PCT/KR2017/006342, dated Aug. 31, 2017.
Office Action from corresponding Japanese Patent Application No. 2018-565661, dated Jun. 16, 2020.

* cited by examiner

| | Mixing proportion of crosslinked hyaluronic acid (%) | Dissolution time of microstructure (sec) |
|---|---|---|
| A | 100 | 100-120 (> 60 sec) |
| B | 80 | 70-80 (> 60 sec) |
| C | 40 | 50-60 |
| D | 20 | 35-45 |
| E | 10 | 10-15 |
| F | 0 | 5-10 |

FIG. 1

HYALURONIC ACID MICROSTRUCTURE HAVING EXCELLENT SOLUBILITY CHARACTERISTICS

CROSS-REFERENCE TO RELATED APPLICATIONS

This application is a national phase application of PCT Application No. PCT/KR2017/006342, filed on Jun. 16, 2017, which claims the benefit and priority to Korean Patent Application No. 10-2016-0074985, filed Jun. 16, 2016. The entire disclosures of the applications identified in this paragraph are incorporated herein by references.

FIELD

The present invention relates to a hyaluronic acid microstructure having excellent dissolution characteristics. More specifically, the present invention relates to a biodegradable microstructure containing crosslinked hyaluronic acid and having excellent dissolution characteristics when penetrating the skin.

BACKGROUND

A drug delivery system (DDS) refers to a series of techniques that delivers a pharmacologically active substance to target sites, such as cells, tissues, internal organs, and entrails, organs, so as to reduce side effects and maximize efficacies of drugs by controlling absorption and release of drugs using various physicochemical techniques. The drug delivery systems are, in addition to a general oral intake type drug delivery system, an inhalation administration type drug delivery system by which a drug is delivered into the lung, a transdermal administration type drug delivery system by which a drug can be locally applied, and the like. Studies have been continuously conducted for efficiently and safely administering drugs while increasing patient compliance according to chemical properties and the purposes of use in vivo of pharmacologically active substances. Of these, the injection therapy has an advantage in that an accurate amount of drug can reach the systemic circulation bloodstream at a high rate, but has disadvantages in that the administration method is inconvenient, some patients may suffer from pain, and frequent injection administration is needed due to a short half-life. The transdermal drug delivery system, compared with the injection administration type, has advantages in that the convenience of a user is increased, drug efficacy can be exerted immediately since a drug is not metabolized in the liver or stomach, a drug with a short half-life can be continuously delivered, and the administration of a drug is easy to stop even in the event of side effects, but has disadvantages in that the release rate of a drug is difficult to accurately control and the system can be applied to only low-molecular weight drugs since high-molecular weight drugs are difficult to penetrate the skin. In order to solve the disadvantages of the injection therapy and transdermal drug delivery system, studies have been actively conducted on a method wherein a fine hole is formed in the skin by using a microstructure (microneedle), which is much smaller and causes less pain compared with a syringe needle, and a drug is delivered via the hole. A microstructure can significantly increase the level of a drug, which can be delivered through the skin, to not only a low-molecular weight drug and a high-molecular weight drug but also a particle, and thus the microstructure has been recently attracting attention as a use in association with a transdermal drug delivery vehicle, and has been developed as various purposes in several fields, such as blood collection, biosensors, and skin care.

As for methods for manufacturing microneedles of the prior art, there are U.S. Pat. No. 6,334,856, "MICRONEEDLE DEVICES AND METHODS OF MANUFACTURE AND USE THEREOF" and Korea Patent No. 10-0793615, "BIODEGRADABLE SOLID MICRONEEDLES AND MANUFACTURING METHOD THEREFOR". The above patents disclose that microneedles are manufactured by injecting a biodegradable viscous substance in a micro-mold manufactured of a curable polymer, followed by drying and de-molding (molding technique), or microneedles are manufactured by coating a biodegradable viscous substance for forming a biodegradable solid microneedle, drawing and drying the coated biodegradable viscous substance on a frame that is patterned in pillars, and then cutting the drawn biodegradable viscous substance (drawing technique). However, such biodegradable polymer microstructures manufactured by the methods of the prior art may be bent or crushed at the time of skin penetration due to relatively low mechanical strength thereof, and especially, in cases where a polymer derivative having high elasticity is used as a raw material, a desired structural shape is not uniformly created through a molding technique or a drawing technique and the mechanical strength of the microstructures necessary for skin penetration is hard to satisfy. Moreover, such microstructures only puncture the skin and cannot be used as mediators to delivering drugs, and therefore, a separate drug delivery system for drug application is needed.

Throughout the specification, many papers and patent documents are used as references, and the citations thereof are represented. The disclosure of the cited papers and patent documents are entirely incorporated by reference into the present specification, and the level of the technical field within which the present invention falls and the details of the present invention are explained more clearly.

SUMMARY

Technical Problem

The present inventors endeavored to solve the problems of the above-described conventional drug delivery systems and microstructures. As a result, the present inventors verified that when a hydrogel formed of crosslinked hyaluronic acid, which is a derivative of hyaluronic acid as a constituent component of the skin, is used as a main ingredient of a microstructure, the microstructure has excellent dissolution characteristics in the skin, the dissolution rate of the microstructure in the skin can be easily controlled depending on the content proportion of the crosslinked hyaluronic acid, the effective ingredient loaded in the microstructure is stably delivered into the skin, and the release rate of the loaded effective ingredient can be easily controlled, and thus the present inventors completed the present invention.

Therefore, an aspect of the present invention is to provide a microstructure containing crosslinked hyaluronic acid and having excellent dissolution characteristics when penetrating the skin.

Other purposes and advantages of the present disclosure will become more obvious with the following detailed description of the invention, claims, and drawings.

Technical Solution

In accordance with an aspect of the present invention, there is provided a skin penetrating microstructure containing, as a main ingredient, i) crosslinked hyaluronic acid or ii) a mixture of crosslinked hyaluronic acid and non-crosslinked hyaluronic acid, wherein, relative to the weight of the overall hyaluronic acid, the content of the crosslinked hyaluronic acid is 5-100% (w/w) and the content of the non-crosslinked hyaluronic acid is 0-95% (w/w).

As used herein, the term "hyaluronic acid" refers to a biodegradable polymer having a linkage structure in which a disaccharide unit composed of N-acetyl glucosamine and glucuronic acid is repeated, and the term is used to mean including all of not only hyaluronic acid but also hyaluronic acid salts (e.g., sodium hyaluronate, potassium hyaluronate, magnesium hyaluronate, and calcium hyaluronate) and mixtures thereof.

As used herein, the term "hydrogel" refers to a three-dimensional structure of hydrophilic polymer retaining a sufficient amount of moisture. For a purpose of the present invention, the hydrogel is formed by characteristics of crosslinked hyaluronic acid.

The present invention can provide various forms of microstructures, and for example, a microneedle, a microblade, a microknife, a microfiber, a microspike, a microprobe, a microbarb, a microarray, or a microelectrode can be provided. According to an embodiment of the present invention, the microstructure of the present invention is a microneedle.

According to an embodiment of the present invention, the microstructure (microneedle) of the present invention has a length of 80-1500 μm.

As used herein, the "penetration" refers to the passing of a protrusion portion of a microstructure through the epidermal layer of the skin when the microstructure is applied to the skin, and preferably the reach of the microstructure up to the dermal layer.

According to an embodiment of the present invention, the microstructure of the present invention shows different dissolution characteristics in an agarose gel depending on the content proportion of crosslinked hyaluronic acid.

Specifically, microstructures of the present invention were manufactured by adding hyaluronic acid to purified water such that crosslinked hyaluronic acid is contained at a mixing proportion of 0%, 10%, 20%, 40%, 80%, or 100% (w/w) relative to the weight of the overall hyaluronic acid (non-crosslinked hyaluronic acid and crosslinked hyaluronic acid) contained in the microstructure, completely dissolving the mixture to prepare a hyaluronic acid hydrogel polymer, mixing 0.1% of methylene blue with the hyaluronic acid hydrogel, and then supplying, injecting, and drying the resultant mixture in a PDMS mold. As a result of observation of the penetration of the microstructure attached to a 3% (w/v) agarose gel in a vertical direction, it was verified that the microstructure dissolved for 5-10 seconds in cases of 0% of crosslinked hyaluronic acid, for 10-15 seconds in cases of 10% of crosslinked hyaluronic acid, for 35-45 seconds in cases of 20% of crosslinked hyaluronic acid, for 50-60 seconds in cases of 40% of crosslinked hyaluronic acid, for 70-80 seconds in cases of 80% of crosslinked hyaluronic acid, and for 100-120 seconds in cases of 100% of crosslinked hyaluronic acid. Therefore, the dissolution rate of the microstructure in an agarose gel is slowly decreased with an increasing mixing proportion of crosslinked hyaluronic acid, and the dissolution rate of the microstructure in an agarose gel is gradually increased with a decreasing mixing proportion of crosslinked hyaluronic acid.

Furthermore, according to an embodiment of the present invention, the microstructure of the present invention has particular dissolution characteristics in the skin when penetrating the skin.

Specifically, according to an embodiment of the present invention, when the microstructure of the present invention is allowed to penetrate the skin by a force of 3 kgf, 60% or less of the length of the microstructure dissolves 10 minutes after skin penetration, 75% or less of the length of the microstructure dissolves 30 minutes after skin penetration, and 85% or less of the length of the microstructure dissolves 60 minutes after skin penetration.

In a case where the crosslinked hyaluronic acid is contained at 15-30% relative to the weight of the overall hyaluronic acid, 50-60% of the length of the microstructure dissolves 10 minutes after skin penetration, 65-75% of the length of the microstructure dissolves 30 minutes after skin penetration, and 70-85% of the length of the microstructure dissolves 60 minutes after skin penetration.

In a case where the crosslinked hyaluronic acid is contained at 30-35% relative to the weight of the overall hyaluronic acid, 45-55% of the length of the microstructure dissolves 10 minutes after skin penetration, 58-68% of the length of the microstructure dissolves 30 minutes after skin penetration, and 65-75% of the length of the microstructure dissolves 60 minutes after skin penetration.

In a case where the crosslinked hyaluronic acid is contained at 35-50% relative to the weight of the overall hyaluronic acid, 40-55% of the length of the microstructure dissolves 10 minutes after skin penetration, 51-61% of the length of the microstructure dissolves 30 minutes after skin penetration, and 55-65% of the length of the microstructure dissolves 60 minutes after skin penetration.

In a case where the crosslinked hyaluronic acid is contained at 50-70% relative to the weight of the overall hyaluronic acid, 35-45% of the length of the microstructure dissolves 10 minutes after skin penetration, 44-54% of the length of the microstructure dissolves 30 minutes after skin penetration, and 48-58% of the length of the microstructure dissolves 60 minutes after skin penetration.

In a case where the crosslinked hyaluronic acid is contained at 70-90% relative to the weight of the overall hyaluronic acid, 30-45% of the length of the microstructure dissolves 10 minutes after skin penetration, 41-51% of the length of the microstructure dissolves 30 minutes after skin penetration, and 45-56% of the length of the microstructure dissolves 60 minutes after skin penetration.

The dissolution rate according to the time of skin penetration time by concentration (content) of crosslinked hyaluronic acid as described above is only exemplified in order to explain that the dissolution rate of the microstructure can be controlled by adjusting the concentration of crosslinked hyaluronic acid. Therefore, the range in the present invention is not necessarily limited to the above range.

Meanwhile, the porcine skin tissue used in the above examples is frequently used as a substitute for human skin tissue since porcine tissue is considered as a material having the highest similarity in the structure and functions, such as metabolic characteristics, of human skin tissue in academia and industries associated with the present microstructure, and especially, the porcine skin tissue shows almost the same degree of similarity as in diffusion characteristics in human skin in a drug transdermal administration and diffusion experiment (Kong R et al., "Characterization of porcine skin as a model for human skin studies using infrared spectroscopic imaging", Analyst. 2011 Jun. 7; 136(11):

2359-66), which provides the results obtained from the porcine skin tissue, but it can be predicted that the porcine skin tissue shows similar results to dissolution characteristics in the human skin tissue.

The concentration of the hyaluronic acid contained as a main ingredient in the microstructure of the present invention is 1-10% (w/v) relative to water or an aqueous solvent constituting i) the crosslinked hyaluronic acid or ii) the hyaluronic acid mixture, and the content of the crosslinked hyaluronic acid is 5-100% (w/w) and the content of the non-crosslinked hyaluronic acid is 0-95% (w/w) relative to the weight of the overall hyaluronic acid.

The water is not particularly limited, but is preferably purified water or sterile water for use as a drug delivery vehicle that directly penetrates the skin to apply a cosmetic agent or deliver a drug.

The aqueous solvent is a generic term for hydrophilic solvents that can be used in mix with water. The aqueous solvent is not particularly limited, but is preferably a physiological saline solution, which may be administered in vivo, such as a phosphate buffer, an acetate buffer, or a tris buffer, in consideration of a use for direct skin penetration.

The molecular weight of the hyaluronic acid contained as a main ingredient in the microstructure of the present invention may be 100-5000 kDa, specifically 200-400 kDa, but is not limited thereto.

According to an embodiment of the present invention, the crosslinked hyaluronic acid of the present invention has a degree of crosslinking of 1-50%. Specifically, the crosslinked hyaluronic acid has a degree of crosslinking of 1-40%, 2-40%, 5-40%, 7-40%, 10-40%, 15-40%, 18-40%, 20-40%, 22-40%, 25-40%, 28-40%, 30-40%, 1-35%, 2-35%, 5-35%, 7-35%, 10-35%, 15-35%, 18-35%, 20-35%, 22-35%, 25-35%, 28-35%, 1-30%, 2-30%, 5-30%, 7-30%, 10-30%, 15-30%, 18-30%, 20-30%, 22-30%, 25-30%, 28-30%, 1-25%, 2-25%, 5-25%, 7-25%, 10-25%, 15-25%, 18-25%, 20-25%, 22-25%, 1-20%, 2-20%, 5-20%, 7-20%, 10-20%, 15-20%, 18-20%, 1-15%, 2-15%, 5-15%, 7-15%, 10-15%, 1-10%, 2-10%, 5-10%, 7-10%, 1-5%, 2-5%, 1-3%, or 2-3%.

The microstructure of the present invention may further contain a biocompatible polymer or an additive.

The biocompatible polymer includes all biocompatible polymers that are ordinarily used in a field of microstructures. Specifically, the biocompatible polymer is at least one polymer selected from the group consisting of carboxymethyl cellulose (CMC), alginic acid, pectin, carrageenan, chondroitin (sulfate), dextran (sulfate), chitosan, polylysine, collagen, gelatin, carboxymethyl chitin, fibrin, agarose, pullulan polylactide, polyglycolide (PGA), polylactide-glycolide copolymer (PLGA), pullulan polyanhydride, polyorthoester, polyetherester, polycaprolactones, polyesteramide, poly(butyric acid), poly(valeric acid), polyurethane, polyacrylate, ethylene-vinyl acetate polymer, acrylic substituted cellulose acetate, non-degradable polyurethane, polystyrene, polyvinyl chloride, polyvinyl fluoride, poly(vinyl imidazole), chlorosulphonate polyolefin, polyethylene oxide, polyvinylpyrrolidone (PVP), polyethylene glycol (PEG), polymethacrylate, hydroxypropyl methylcellulose (HPMC), ethylcellulose (EC), hydroxypropyl cellulose (HPC), cyclodextrin, copolymers of monomers forming these polymers, and cellulose.

The additive includes all additives that are ordinarily used in a field of microstructures. Specifically, the adhesive is at least one adhesive selected from the group consisting of silicone, polyurethane, a physical adhesive (Gecko), polyacryl, ethyl cellulose, hydroxy methyl cellulose, ethylene vinyl acetate, and polyisobutylene.

The microstructure of the present invention is manufactured by dissolving various biocompatible polymers including hyaluronic acid, or an adhesive, in water or an aqueous solvent and then supplying, injecting, and drying the resultant solution in a polydimethyl silozane (PDMS) mold. According to an embodiment of the present invention, the biocompatible polymer or adhesive supplied into the PDMS is contained at a concentration of 1-10% (w/v) in water or an aqueous solvent, but is not limited thereto.

Alternatively, the microstructure containing crosslinked hyaluronic acid as a main ingredient of the present invention may be manufactured by employing any micro-mold manufacturing method in the art.

In addition, the microstructure of the present invention may contain a physiologically active substance or a substance for skin improvement. Specific examples thereof include an anti-inflammatory agent, a pain reliever, an anti-arthritic agent, an antispasmodic, an anti-depressive agent, an antipsychotic, a tranquilizer, an anti-anxiety drug, a narcotic antagonist, an anti-Parkinson's disease drug, a cholinergic agonist, an anti-cancer drug, an anti-angiogenic agent, an immunosuppressive agent, an antiviral agent, an antibiotic, an appetite suppressant, a pain reliever, an anticholinergic agent, an anti-histamine, an anti-migraine agent, a hormonal agent, a coronary, cerebral, or peripheral vasodilator, a contraceptive, an anti-thrombotic agent, a diuretic, an anti-hypertensive agent, a cardiovascular therapeutic agent, and a cosmetic ingredient (e.g., an anti-wrinkle agent, a skin aging inhibitor, and a skin whitening agent), but are not limited thereto.

The microstructure of the present invention can load a pharmacologically active substance as such, can effectively release and diffuse the loaded pharmacologically active substance when penetrating the skin, and can control the release and diffusion rates of the pharmacologically active substance depending on the proportions of crosslinked hyaluronic acid and non-crosslinked hyaluronic acid constituting the microstructure. Specifically, as for an example of the present invention, a microstructure manufactured by mixing calcein as a fluorescent substance with a crosslinked hyaluronic acid hydrogel polymer such that the calcein is contained at 5% (w/v) was allowed to vertically penetrate the porcine skin for 1, 30, and 120 minutes. As a result, the microstructure dissolved at a fast rate 1-30 minutes after skin penetration and a fluorescent signal of calcein was released, diffused, and maintained at a fast rate, and the fluorescent signal of calcein was strongly observed even 120 minutes after skin penetration of the microstructure.

The microstructure of the present invention can be manufactured by chemically binding a pharmacologically active substance to hyaluronic acid as a main ingredient, and can exhibit excellent dissolution characteristics when penetrating the skin and can effectively deliver the pharmacologically active substance. As for another example of the present invention, a microstructure of the present invention was manufactured by using a fluorescent substance (fluorescein)-conjugated hyaluronic acid, and the manufactured microstructure was allowed to penetrate the skin. As a result, the tip portion of a needle started to dissolve, and non-crosslinked hyaluronic acid started to dissolve immediately after skin penetration of the needle, and dissolved at a very fast rate from skin penetration to about 30 minutes. Furthermore, it could be verified that, due to a slow dissolution rate of crosslinked hyaluronic acid, a fluorescent signal was maintained for 120 minutes or longer while the shape of the microstructure was maintained even after 120 minutes.

In addition, according to an embodiment of the present invention, the microstructure of the present invention has a degree of elasticity appropriate for skin penetration. More specifically, the microstructure of the present invention has a Young's modulus of 0.4-0.7 N/100 μm.

The Young's modulus is the coefficient of elasticity indicating a relationship between strain and pressure occurring in an object, and as for a one-dimensional example, when the Young's modulus is E, stress=E×strain. The Young's modulus is an intrinsic property of an object, and the Young's modulus is used to predict the degree of strain of the object when the pressure applied to the object is known, and vice versa.

In examples 4 to 6 of the present invention, according to the experimental results of skin penetration on porcine skin, the range of the Young's modulus corresponds to a range of mechanical strength sufficient for penetrating the porcine skin.

The microstructure of the present invention has high mechanical strength since 80% or more of the height of the microstructure penetrates the skin, and according to the example, the mechanical strength was 80-100 (penetration ratio, %).

As described above, the microstructure of the present invention has very excellent dissolution characteristics when penetrating the skin, and the dissolution rate of the microstructure is easy to control by adjusting the content (mixing) proportion of crosslinked hyaluronic acid. In addition, a pharmacologically active substance can be easily loaded in a manner in which the pharmacologically active substance is mixed, hyaluronic acid chemically linked to a pharmacologically active substance is used, or the like when the microstructure is manufactured; the loaded pharmacologically active substance can be effectively released and diffused when the microstructure penetrates the skin, and thus an effective ingredient can be stably delivered into the skin; and the dissolution rate of hyaluronic acid and the release and diffusion rates of the effective ingredient can be easily controlled by adjusting the content of crosslinked hyaluronic acid. Therefore, the microstructure of the present invention can be effectively used as a transdermal delivery vehicle for a pharmacologically active substance or a substance for skin improvement.

Advantageous Effects

Features and advantages of the present invention are summarized as follows.

(a) The present invention provides a microstructure comprising i) crosslinked hyaluronic acid or ii) a mixture of crosslinked hyaluronic acid and non-crosslinked hyaluronic acid and dissolving in the skin at the time of skin penetration.

(b) When the microstructure of the present invention is allowed to penetrate the skin, the dissolution characteristics of the microstructure in the skin are excellent, the dissolution rate of the microstructure in the skin can be easily controlled according to the content proportion of the crosslinked hyaluronic acid. Furthermore, the effective ingredient loaded in the microstructure can be stably delivered into the skin while the release rate of the loaded effective ingredient can be easily controlled. Therefore, the microstructure of the present invention can be effectively used as a transdermal delivery vehicle for a pharmacologically active substance or a substance for skin improvement.

BRIEF DESCRIPTION OF THE DRAWINGS

FIG. 1 shows the dissolution time of a microstructure of the present invention depending on the mixing proportion of crosslinked hyaluronic acid.

DETAILED DESCRIPTION

Figure 2A:
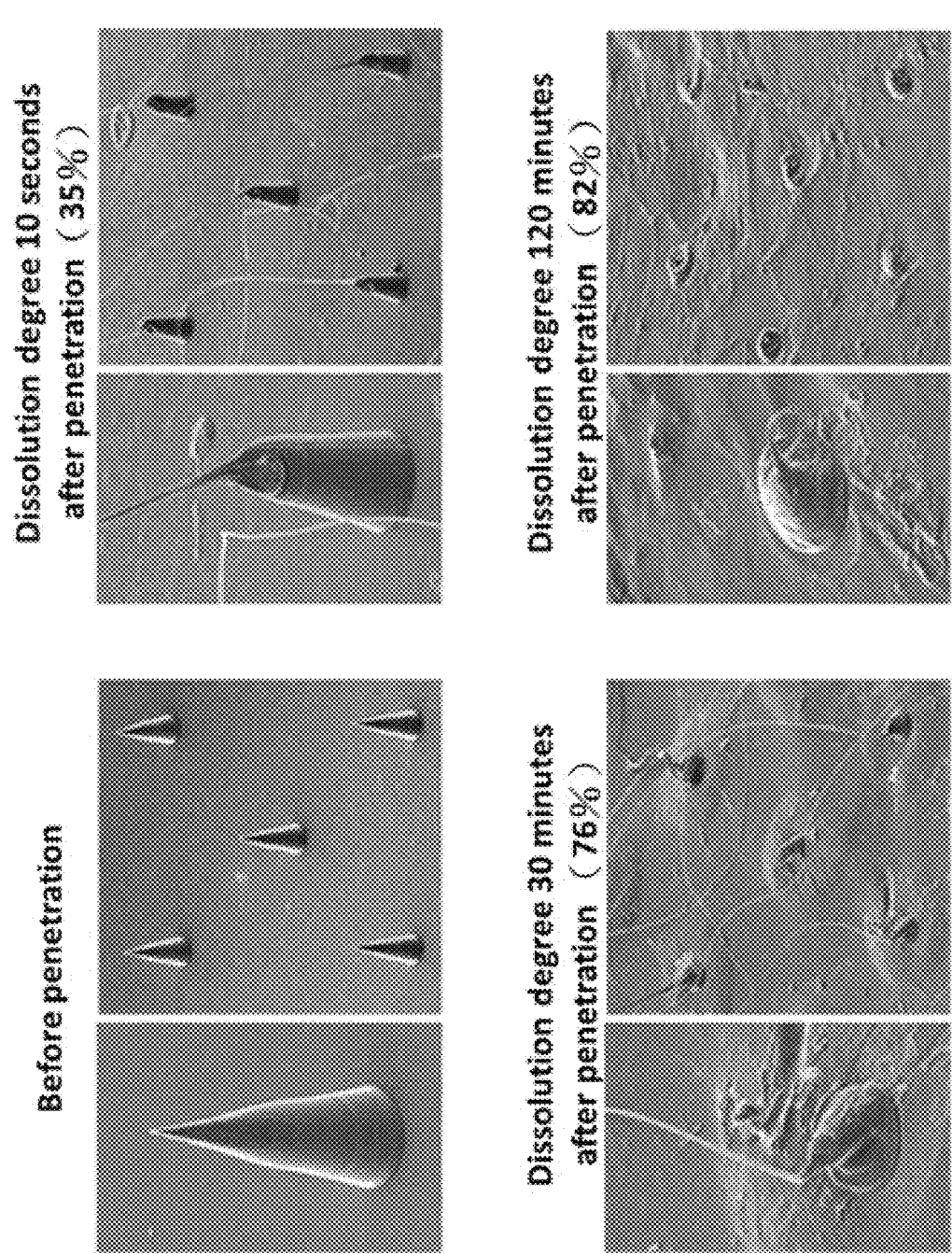
FIG. 2a shows scanning electron microscopy (SEM) observations of the length of a microstructure of the present invention remaining according to the penetration time (before penetration, 10 seconds, 30 minutes, and 120 minutes) after the microstructure was allowed to penetrate the porcine skin.

Hereinafter, the present invention will be described in detail with reference to examples. These examples are only for illustrating the present invention more specifically, and it will be apparent to those skilled in the art that the scope of the present invention is not limited by these examples.

Examples

Throughout the present specification, the term "%" used to express the concentration of a specific material, unless otherwise particularly stated, refers to (wt/wt) % for solid/solid, (wt/vol) % for solid/liquid, and (vol/vol) % for liquid/liquid.

Example 1: Experiment of Dissolution Rates when Microstructures Containing Crosslinked Hyaluronic Acid Penetrate Agarose Gel

Example 1-1: Manufacturing of Microstructures Containing Crosslinked Hyaluronic Acid A positive or negative master mold was manufactured by using photography and etching techniques performed on a silicon wafer, and then a final negative mold was manufactured from the mast mold using curable silicone (polydimethylsiloxane, PDMS).

Hyaluronic acid having an average molecular weight of 360 kDa (molecular weight range: 240-490 kDa) as a biocompatible polymer was completely dissolved in alkaline water (0.25 N NaOH), and then, for crosslinkage thereof, 1,4-butanediol diglycidyl ether (BDDE) as a cross-linking agent was added thereto, thereby preparing crosslinked hyaluronic acid. The prepared crosslinked hyaluronic acid was added to purified water such that the crosslinked hyaluronic acid was contained at mixing proportions of 0%, 10%, 20%, 40%, 80%, and 100% (w/w) relative to the weight of the overall hyaluronic acid (non-crosslinked hyaluronic acid and crosslinked hyaluronic acid), followed by complete dissolution, to prepare crosslinked/non-crosslinked hyaluronic acid hydrogel polymers. For example, a hyaluronic acid hydrogel polymer containing crosslinked hyaluronic acid at a mixing proportion of 10% (w/w) relative to the weight of the overall hyaluronic acid can be prepared when 0.5 g of crosslinked hyaluronic acid and 4.5 g of non-crosslinked hyaluronic acid were dissolved in 100 ml of purified water. The prepared thus hyaluronic acid hydrogel polymers were supplied, injected, and dried in a PDMS micromold, followed by demolding, thereby manufacturing microstructures of the present invention.

Example 1-2: Experiment of Dissolution Rate when Microstructures Containing Crosslinked Hyaluronic Acid Penetrate Agarose Gel In order to investigate the dissolution rate of a microstructure at the time of agarose gel penetration, blue hyaluronic acid microstructures were manufactured by mixing the same volume of 0.1% methylene blue with crosslinked/non-crosslinked hyaluronic acid hydrogels, which were prepared by containing crosslinked hyaluronic acid at weight proportions of 0-100% (w/w) relative to the weight of the overall hyaluronic acid in example 1-1, and then supplying, injecting, and drying the resultant mixtures in a PDMS micromold, followed by demolding.

Then, 0.75 g of agarose powder was added to 25 ml of distilled water, and dissolved therein through heating, followed by cooling, to prepare a 3% (w/v) agarose gel, which was cut into an appropriate size (about 0.8 cm×1 cm).

Each of the prepared microstructures containing methylene blue was cut into a width of 0.1-0.15 cm, and then attached on the agarose gel in a vertical direction so as to allow the microstructure to penetrate the gel. A phenomenon in which the microstructure was dissolved in the agarose gel according to the proportion of crosslinked hyaluronic acid contained in the microstructure was observed using a microscope (Sunny SZMN, 40 magnification or higher) for 2 minutes.

The results are shown FIG. 1.

As shown in FIG. 1, it can be seen that the higher the mixing proportion of crosslinked hyaluronic acid, the longer the time for the microstructure to dissolve, and the lower the mixing proportion of crosslinked hyaluronic acid, the shorter the time for the microstructure to dissolve. Therefore, the dissolution rate of the microstructure of the present invention can be controlled by adjusting the mixing proportion of the crosslinked hyaluronic acid.

Example 2: Experiment of Dissolution Rate when Microstructure Containing 50% (w/w) of Crosslinked Hyaluronic Acid Penetrates Porcine Skin In order to investigate dissolution characteristics of the microstructure of the present invention at the time of skin penetration, the microstructure of the present invention was manufactured by the same method as in example 1 except that the crosslinked hyaluronic acid and the non-crosslinked hyaluronic acid were contained at the same weight proportion. The dissolution rate of the manufactured microstructure was compared by allowing the microstructure to penetrate (be inserted) into the porcine skin for a predetermined time using predetermined force and then checking the degrees of strain before and after the penetration.

Example 2-1: Dissolution Rate on the Basis of Length of Microstructure

Each of the manufactured microstructures was cut into 0.7 cm×0.7 cm, and then was allowed to penetrate the porcine skin in a vertical direction by applying a force of 5 kgf for 10 seconds to 120 minutes. The dissolution rate at the time of penetration was measured by observing a penetration portion of the microstructure via an optical microscope and then checking the degrees of strain of the microstructure before and after skin penetration using a scanning electron microscope (SEM, JEOL JSM-7500F) with regard to length and volume before the penetration, 10 seconds after the penetration, 10 minutes after the penetration, 20 minutes after the penetration, 30 minutes after the penetration, 60 minutes after the penetration, and 120 minutes after the penetration.

Figure 3A:
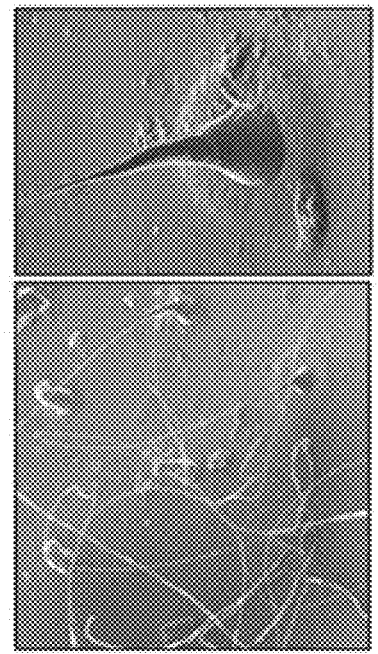
FIG. 3a shows scanning electron microscopy (SEM) observations of the volume of a microstructure of the present invention remaining according to the penetration time (before penetration, 10 minutes, 20 minutes, and 30 minutes) after the microstructure was allowed to penetrate into the porcine skin.
Figure 3A:
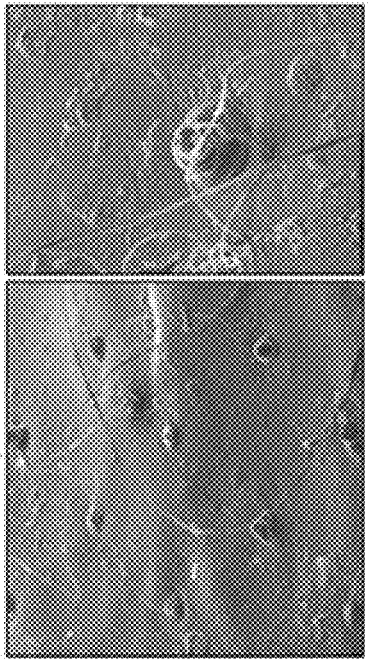
Figure 3A:
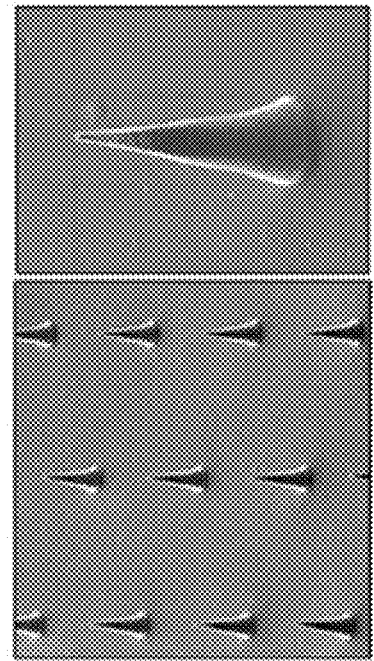
Figure 3A:
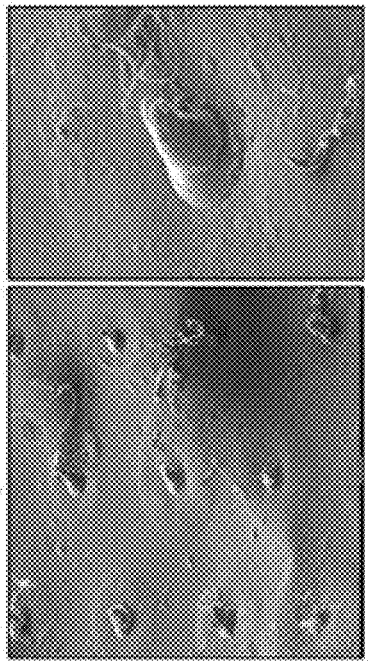

The experimental results of dissolution rate of the microstructure of the present invention according to the length change of the microstructure remaining after the porcine skin penetration are shown in Table 1 and FIGS. 2a and 3a.

TABLE 1

| Penetration time | Before penetration | 10 seconds after penetration | 10 minutes after penetration | 20 minutes after penetration | 30 minutes after penetration | 60 minutes after penetration | 120 minutes after penetration |
|---|---|---|---|---|---|---|---|
| Solubility depending on penetration length | 0% | 35% | 52% | 70% | 76% | 78% | 82% |

As shown in Table 1 and FIGS. 2a and 3a, 35% of the total length of the structure dissolved 10 seconds after the porcine skin penetration, 52% dissolved 10 minutes after the penetration, 70% dissolved 20 minutes after the penetration, 76% dissolved 30 minutes after the penetration, 78% dissolved 60 minutes after the penetration, and 82% dissolved 120 minutes after the penetration.

Example 2-2: Dissolution Rate on the Basis of Volume of Microstructure

Figure 2B:
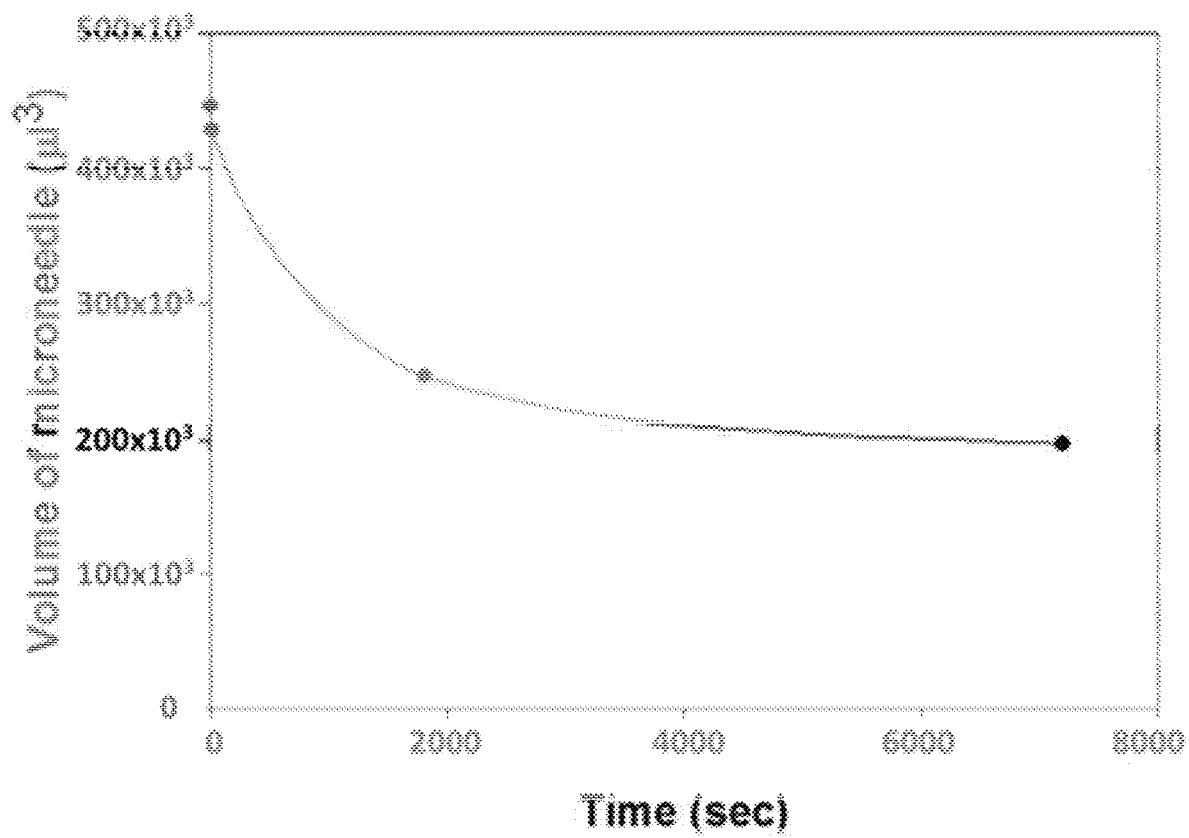
FIG. 2b is a graph showing a dissolution rate on the basis of a volume change of the microstructure remaining after skin penetration.
Figure 3B:
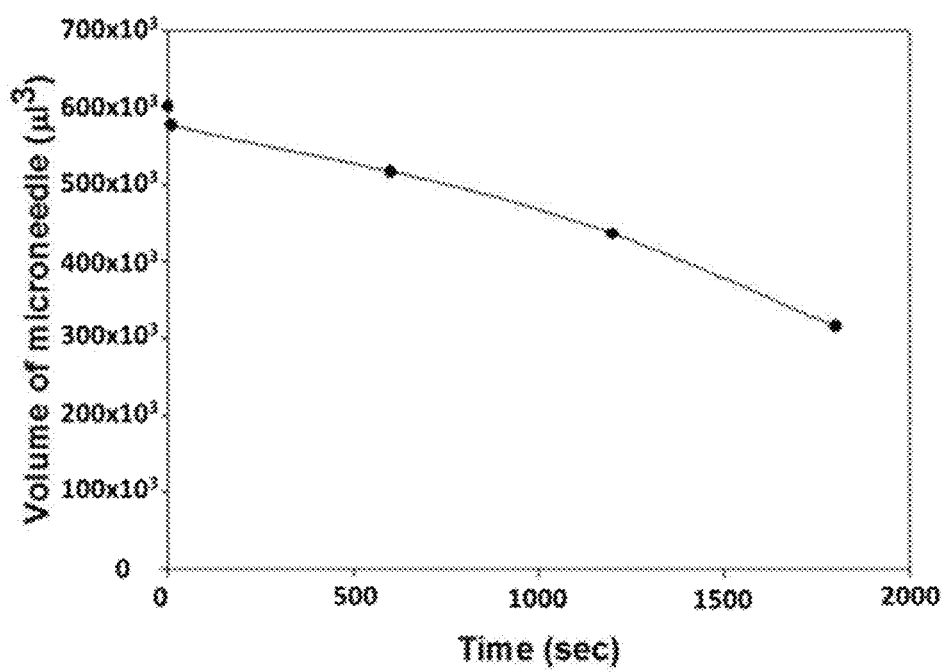
FIG. 3b is a graph showing a dissolution rate on the basis of a volume change of the microstructure remaining after skin penetration.
Figure 4A:
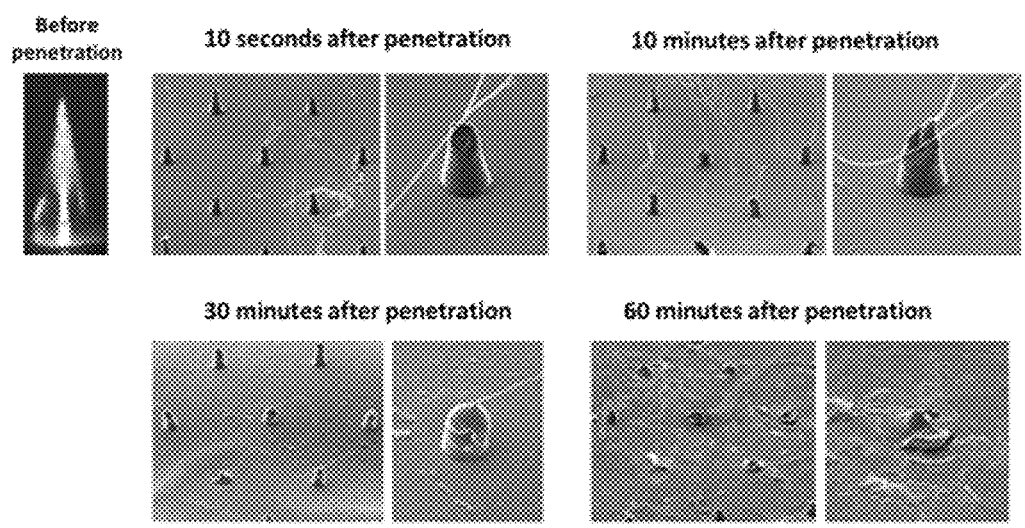
FIGS. 4a, 4b, 4c, 4d, 4e and 4f show scanning electron microscopy observations of the lengths of the microstructures, which contain crosslinked hyaluronic acid at different mixing proportions remaining according to the penetration time (before penetration, 10 seconds, 10 minutes, 30 minutes, and 60 minutes) after the microstructures were allowed to penetrate the porcine skin.
Figure 4B:
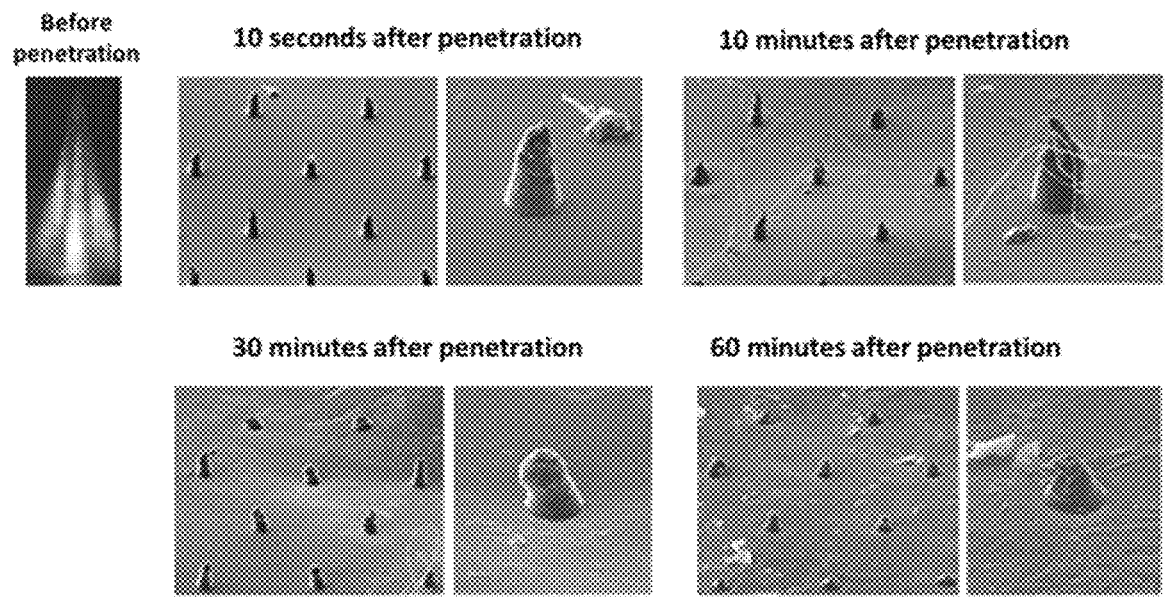
Figure 4C:
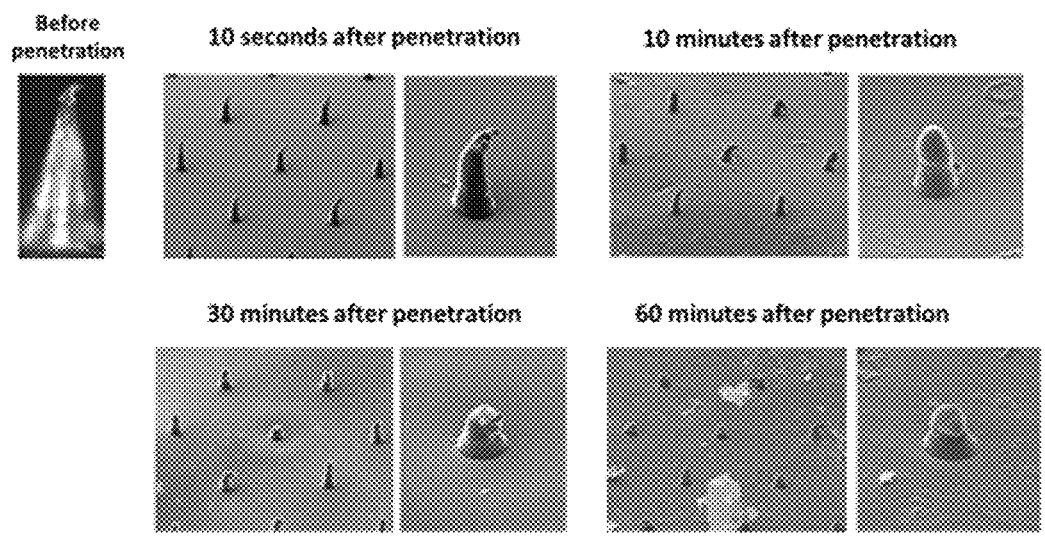
Figure 4D:
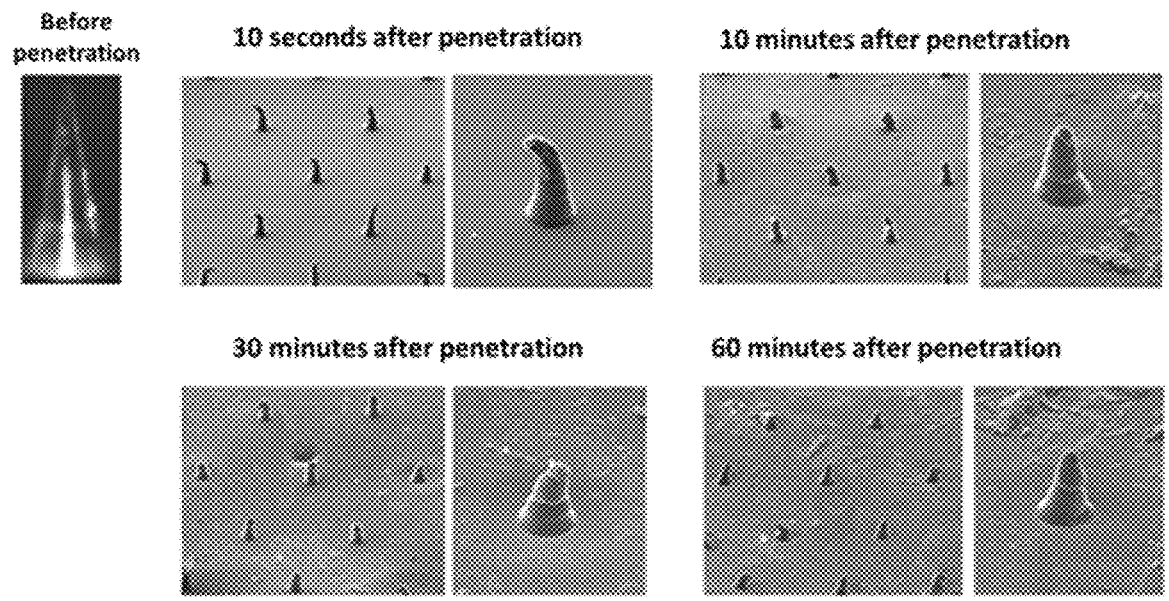
Figure 4E:
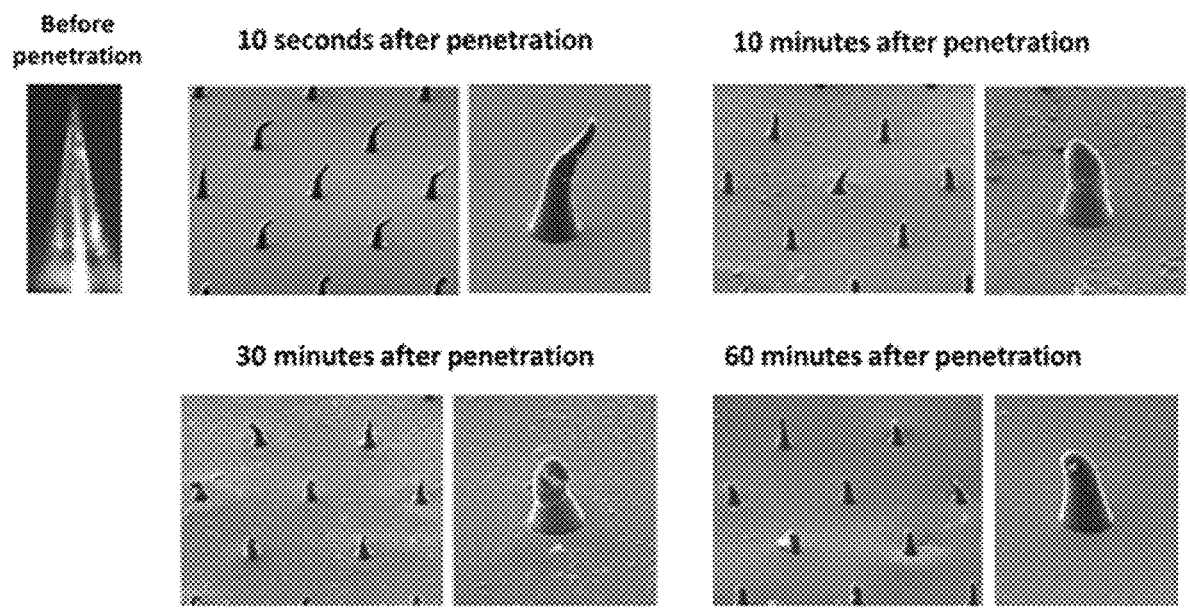
Figure 4F:
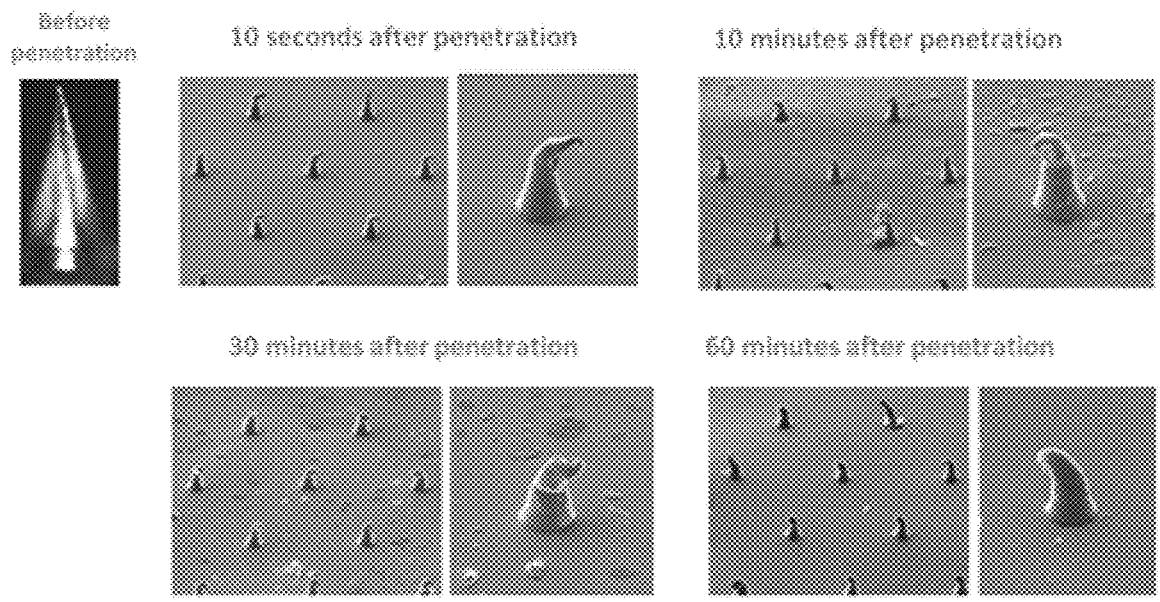
Figure 5A:
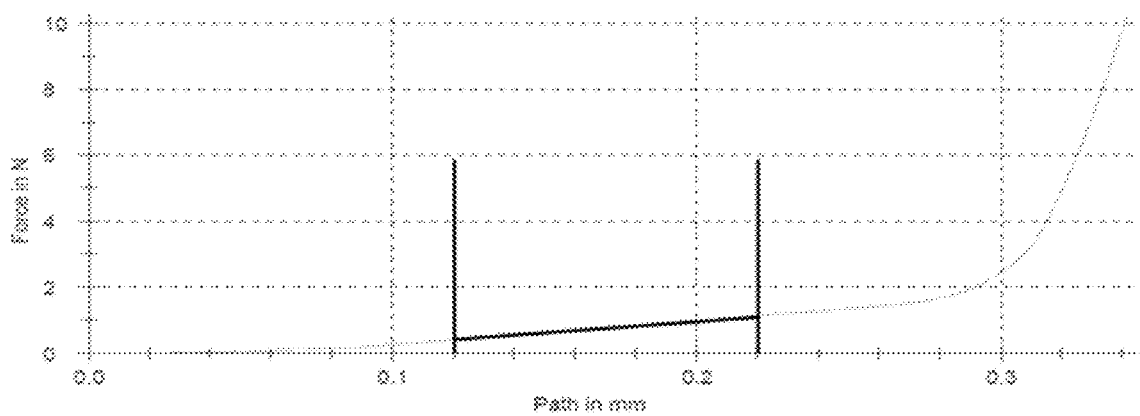
FIGS. 5a, 5b, 5c, 5d, 5e and 5f are graphs confirming strain patterns of structures containing crosslinked hyaluronic acid at different mixing proportions of 0%, 20%, 33%, 40%, 60%, and 80% when particular force is applied to the microstructures using a force displacement equipment.
Figure 5B:
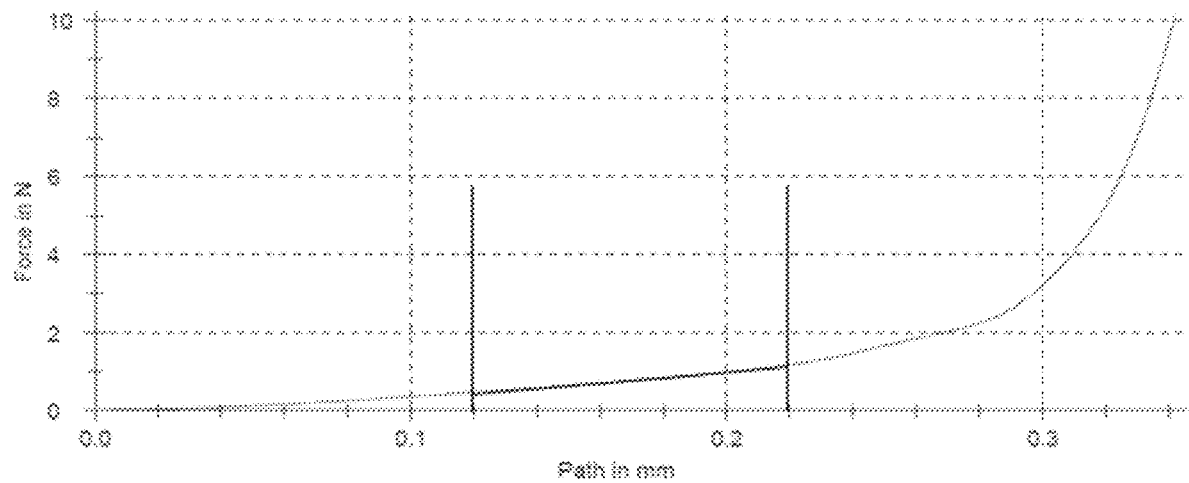
Figure 5C:
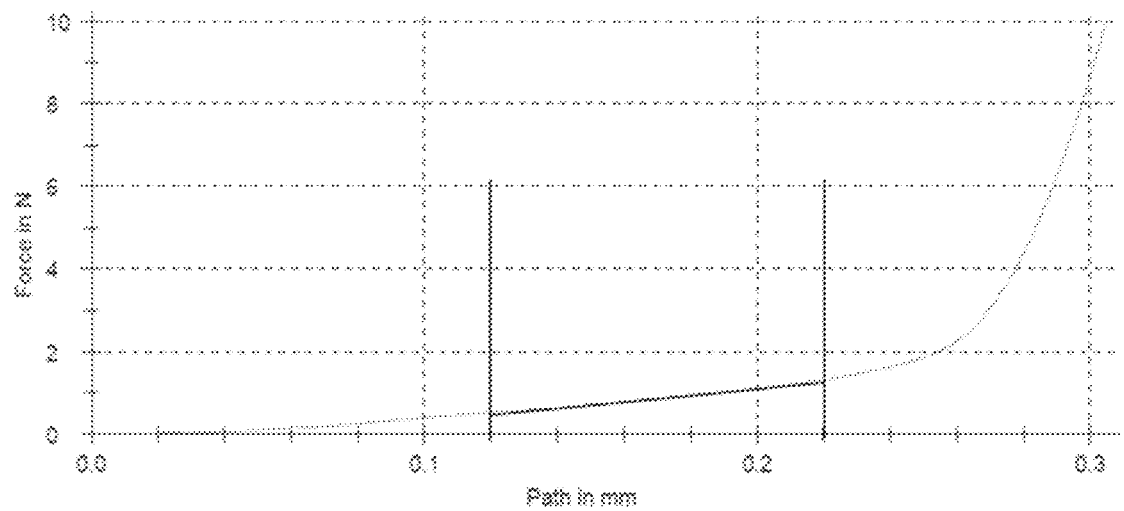
Figure 5D:
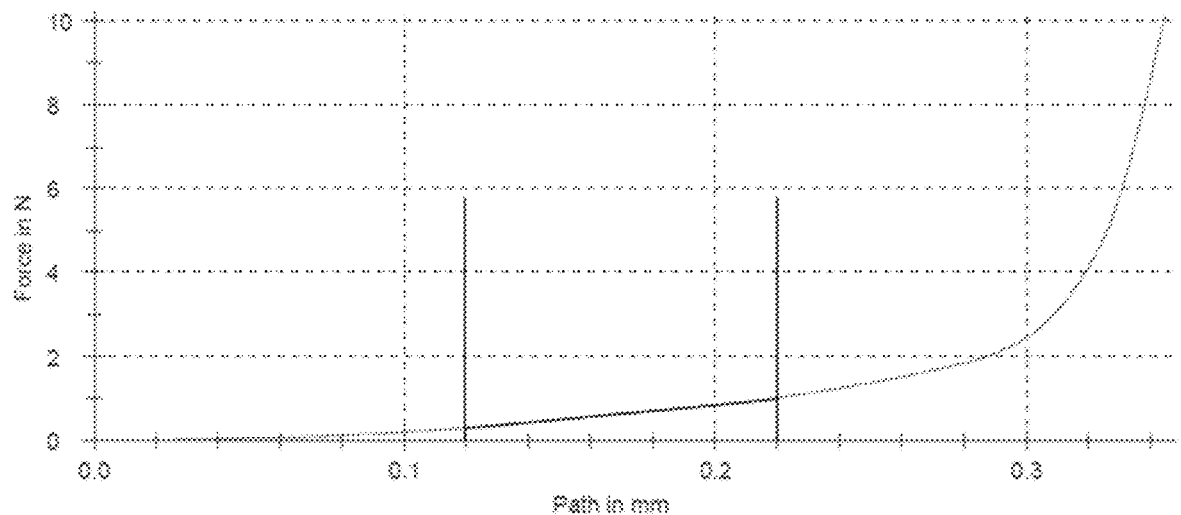
Figure 5E:
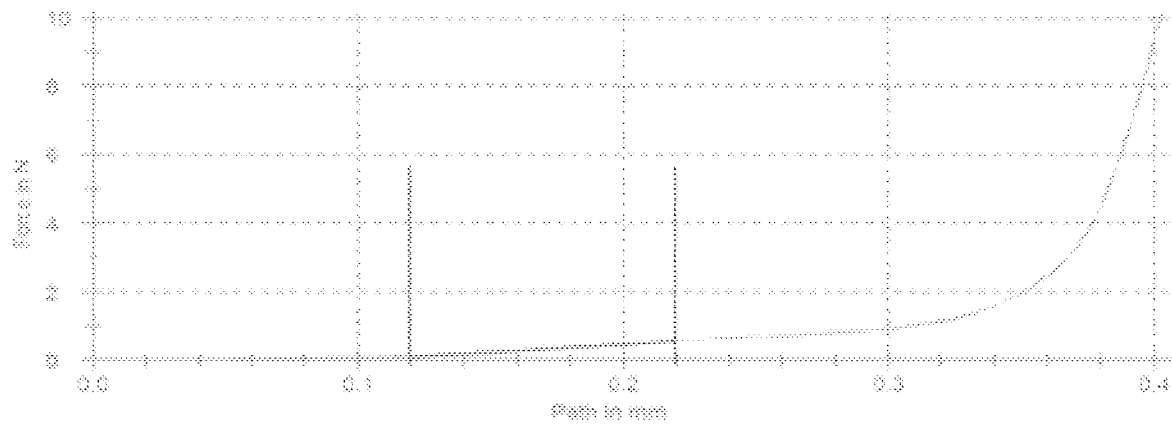
Figure 5F:
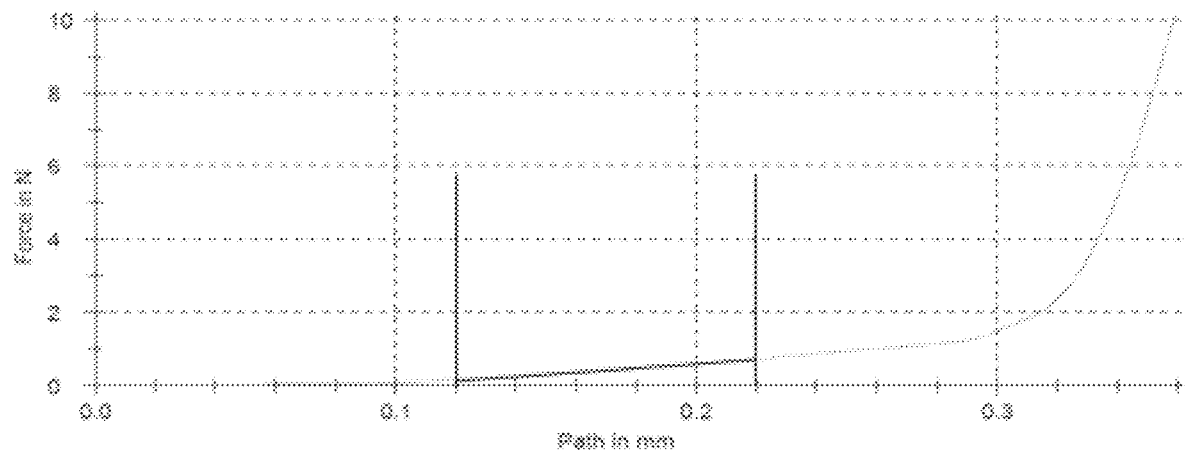

The dissolution rate according the volume of the microstructure of the present invention remaining after the porcine skin penetration was measured, and the experimental results are shown in Table 2 and FIGS. 2b and 3b.

TABLE 2

| Penetration time | Before penetration | 10 seconds after penetration | 10 minutes after penetration | 20 minutes after penetration | 30 minutes after penetration | 120 minutes after penetration |
|---|---|---|---|---|---|---|
| Solubility depending on penetration volume | 0% | 4% | 15% | 30% | 45-48% | 56% |

As shown in Table 2 and FIGS. 2b and 3b, 15% of the total volume continuously dissolved 10 minutes after the penetration at a fast rate, 30% dissolved 20 minutes after the penetration, 45-48% dissolved 30 minutes after the penetration, and then 56% of the total volume dissolved 120 minutes after the penetration, indicating slow gradual dissolution.

Therefore, it can be seen that when the microstructure of the present invention containing crosslinked hyaluronic acid is applied to the human skin, the microstructure can provide a prompt effect until 30 minutes after the penetration since the initial dissolution rate of the non-crosslinked hyaluronic acid is very fast, and then can continuously provide a predetermined effect from 30 minutes after the penetration since the crosslinked hyaluronic acid is slowly dissolved Therefore, the microstructure of the present invention can be effectively used for application to the skin.

Example 3: Comparative Experiment of Dissolution Rate when Microstructures Containing Crosslinked Hyaluronic Acid at Different Proportions Penetrate Porcine Skin In order to investigate the dissolution characteristics of the microstructures of the present invention at the time of skin penetration, crosslinked/non-crosslinked hyaluronic acid hydrogel polymers were prepared by adding crosslinked hyaluronic acid to purified water such that the crosslinked hyaluronic acid was contained at mixing proportions of 0%, 20%, 33%, 40%, 60% and 80% (w/w) relative to the weight of the overall crosslinked hyaluronic acid (non-crosslinked hyaluronic acid and crosslinked hyaluronic acid), followed by complete dissolution, by the same method as in example 1.

Each of the microstructures manufactured by using the polymers was cut into 0.7 cm×0.7 cm, and then was allowed to penetrate the porcine skin in a vertical direction by applying a force of 3 kgf for 10 seconds to 60 minutes. The dissolution rate at the time of penetration was measured by observing a penetration portion of the microstructure and the microstructure before the skin penetration via an optical microscope and then checking the degrees of strain of the microstructure, with regard to length, before the penetration, 10 seconds after the penetration, 10 minutes after the penetration, 30 minutes after the penetration, and 60 minutes after the penetration, using a scanning electron microscope.

The experimental results of dissolution rate of the microstructure of the present invention according to the length change of the microstructure remaining after the porcine skin penetration are shown in Table 3 and FIG. 4.

TABLE 3

| Mixing proportion | Solubility depending on penetrated length by penetration time | | | | |
|---|---|---|---|---|---|
| (%, w/w) of crosslinked hyaluronic acid | Before penetration | 10 seconds after penetration | 10 minutes after penetration | 30 minutes after penetration | 60 minutes after penetration |
| 0 | 0% | 49% | 59% | 72% | 84% |
| 20 | 0% | 45% | 56% | 67% | 76% |
| 33 | 0% | 40% | 50% | 63% | 69% |
| 40 | 0% | 38% | 51% | 56% | 60% |
| 60 | 0% | 30% | 40% | 49% | 53% |
| 80 | 0% | 29% | 37% | 46% | 51% |

As shown in Table 3 and FIGS. 4a to 4f, as the mixing proportion of the crosslinked hyaluronic acid increased, the dissolution rate at the time of skin penetration was slower, and 72%, 67%, 63%, 56%, 49%, and 46% of the total length of the structure were dissolved according to the mixing proportions of crosslinked hyaluronic acid, 0%, 20%, 33%, 40%, 60%, and 80% 30 minutes after the porcine skin penetration.

Therefore, the microstructure containing crosslinked hyaluronic acid of the present invention can control the time to show useful effects for skin care, such as skin moisturizing and anti-wrinkling effects, since the dissolution time of the microstructure in the skin can be controlled by adjusting the mixing proportion of the crosslinked hyaluronic acid when the microstructure was applied to human skin. Furthermore, when an effective ingredient, such as a skin care functional ingredient or a drug, was contained in the microstructure, the microstructure can be effectively used for appropriately controlling the release rate of the effective ingredients into the skin (controlled release).

Example 4: Comparative Experiment of Mechanical Strength of Microstructures Containing Crosslinked Hyaluronic Acid at Different Mixing Proportions In order to investigate mechanical strength characteristics of the microstructure of the present invention at the time of skin penetration, the strain patterns of the microstructure were checked by a force displacement equipment (Zwick/Roell, Germany) when a particular range of force was applied.

By the same method as in example 1, hyaluronic acid was added to purified water such that crosslinked hyaluronic acid was contained at mixing proportions of 0%, 20%, 33%, 40%, 60%, and 80% (w/w) relative to the weight of the overall hyaluronic acid (non-crosslinked hyaluronic acid and crosslinked hyaluronic acid), followed by complete dissolution, to prepare crosslinked/non-crosslinked hyaluronic acid hydrogel polymers.

The microstructures manufactured by the polymers were used to prepare 2×2 structure samples (a total of four structures). The microstructure samples by mixing proportion were mounted on the force displacement equipment, and a force in the range of 0-10 N was applied thereto, specifically to the strained sections of the microstructure, from the tip portion to 100-200 μm, and were observed and compared. In addition, the Young's moduli (N/100 μm) of the structures by mixing portion were measured and compared.

As shown in FIG. 5, slight changes in the force displacement pattern could be observed as the mixing proportion of crosslinked hyaluronic acid varied. The strain of the structure was observed for a force range of 0.3-0.5 N to 0.9-1.3 N, according to the mixing portion of crosslinked hyaluronic acid, in mixing portions of 0%, 20%, 33%, and 40%, and for a force range of 0.1-0.2 N to 0.6-0.7 N in mixing portions of 60% and 80%.

TABLE 4

| | Mixing proportion (%, w/w) of crosslinked hyaluronic acid | | | | | |
|---|---|---|---|---|---|---|
| | 0 | 20 | 33 | 40 | 60 | 80 |
| Young's modulus (N/100 μm) | 0.35 | 0.5 | 0.53 | 0.66 | 0.43 | 0.44 |

Figure 6:
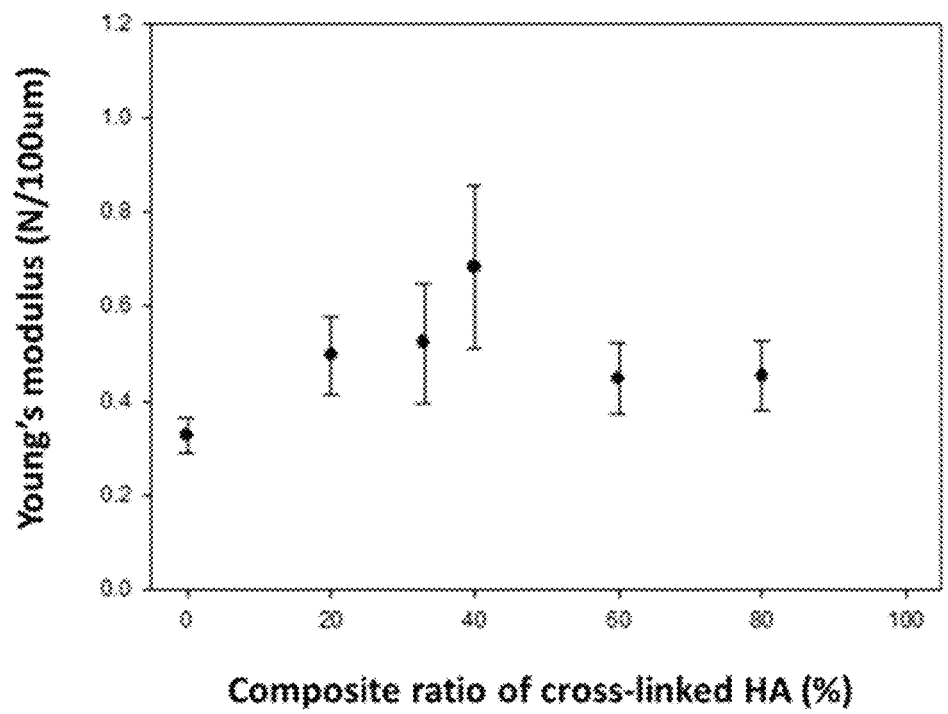
FIG. 6 is a graph obtained by measuring Young's moduli (N/100 μm) of structures containing crosslinked hyaluronic acid at different mixing proportions when particular force is applied to the structures using a force displacement equipment.

As shown in FIG. 6 and Table 4, there was not a large difference in Young's modulus of the structure by mixing proportion, and the Young's moduli were 0.35, 0.5, 0.53, and 0.66 in mixing proportions of cross-liked hyaluronic acid of 0%, 20%, 33%, and 40%, respectively, and 0.43 and 0.44 in the mixing proportions of 60% and 80%, respectively.

The above results could confirm that the microstructure of the present invention had strength and elasticity sufficient for skin penetration in all the content ranges of crosslinked hyaluronic acid. Therefore, it can be seen that through the adjustment of the content of crosslinked hyaluronic acid in the microstructure of the present invention, the dissolution rate of the microstructure and the release rate of the effective ingredient contained in the microstructure could be easily controlled without affecting the strength of the microstructure.

Example 5: Experiment of Diffusion Pattern and Diffusion Rate when Fluorescent Substance (Calcein) Penetrate Skin after being Loaded in Present Microstructure In order to investigate usability of the microstructure of the present invention as a drug delivery vehicle, a fluorescent substance was loaded in the microstructure of the present invention, and then the diffusion pattern and diffusion rate of the fluorescent substance, including the penetration depth, at the time of porcine skin penetration, were checked.

A fluorescent substance, calcein (Sigma Aldrich), was mixed with a crosslinked hyaluronic acid polymer in which crosslinked hyaluronic acid was contained at a proportion of 35% (w/w) relative to the weight of the overall hyaluronic acid, such that the calcein is contained at 5% (w/v) in the crosslinked hyaluronic acid polymer, and then the resultant mixture was supplied, injected, and dried in a mold, thereby manufacturing a microstructure (microneedle) loading calcein therein with a height of 265 μm. The microstructure sample was cut into 0.7 cm×0.7 cm before use, and then allowed to penetrate the porcine skin by a vertical application of a force of 5 kgf for 1 minute, 30 minutes, and 120 minutes. The fluorescent substance remaining on the porcine skin was observed using a confocal microscope (Nikon, ECLIPSE TE2000-E) to check the penetration depth and the diffusion pattern with time.

Figure 7A:
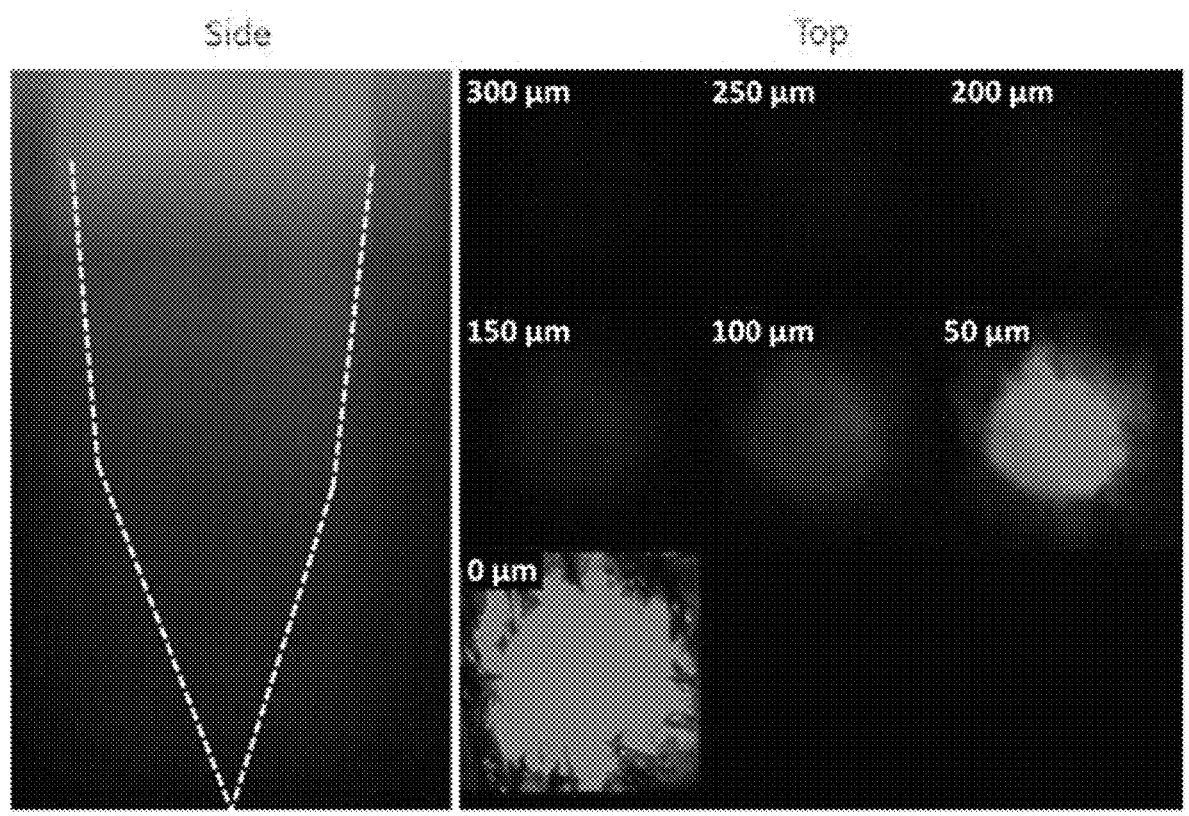
FIGS. 7a, 7b and 7c show the diffusion pattern of a fluorescent substance (calcein) according to the penetration time (1 minute, 30 minutes, and 120 minutes) after a microstructure of the present invention loading the fluorescent substance was allowed to penetrate the porcine skin.
Figure 7B:
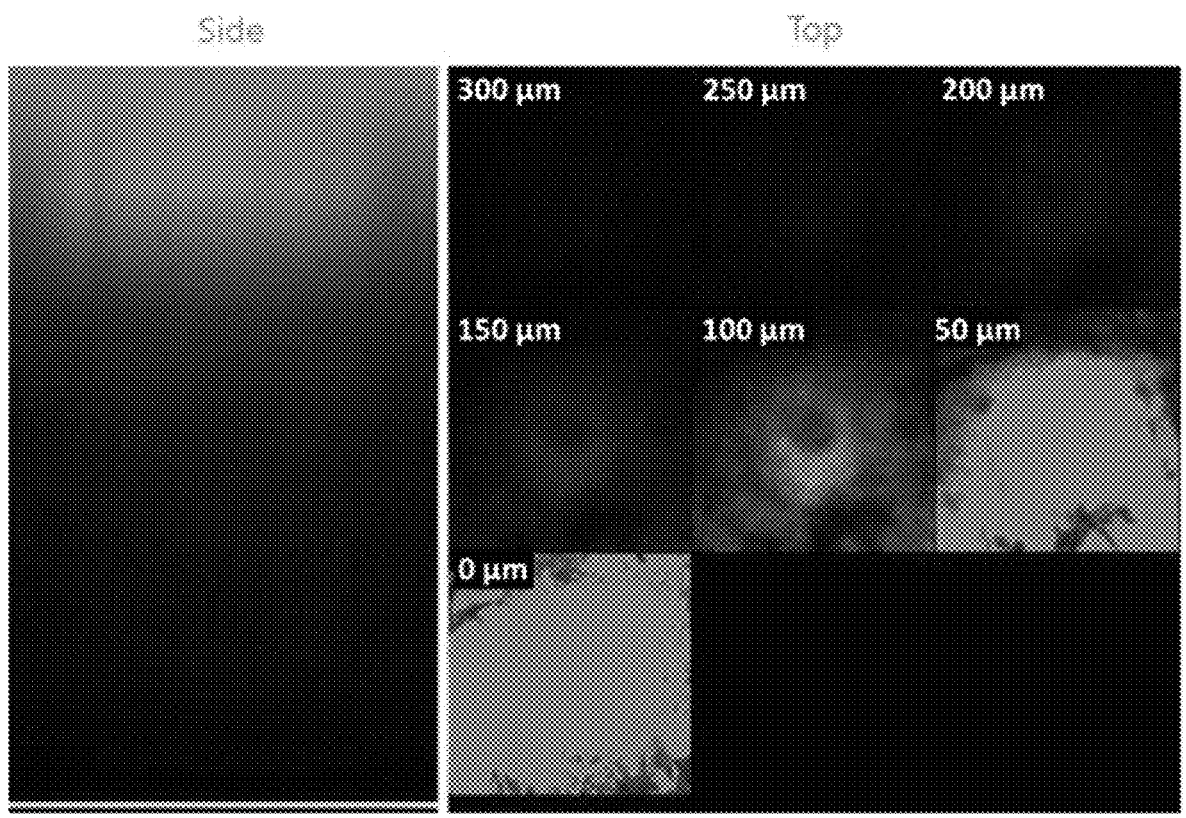
Figure 7C:
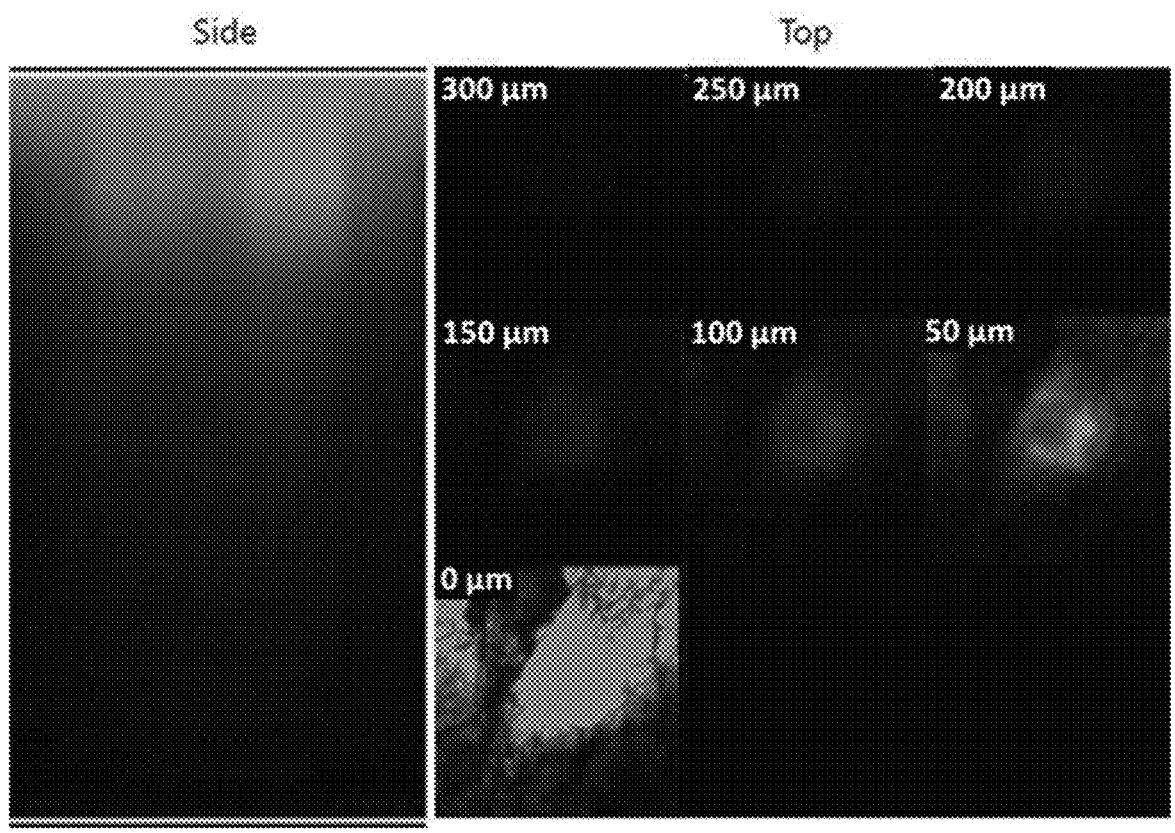

The results are shown in FIGS. 7a to 7c.

As shown in FIGS. 7a to 7c, skin penetration was made to 80% or more of the total needle length (265 μm) 1 minute after skin penetration, and a tip portion of the needle started to dissolve, and the loaded drug calcein was diffused. It was observed that most of the fluorescent signal of calcein was maintained even 30 minutes after the penetration. These results were thought to be due to the non-crosslinked hyaluronic acid with calcein loaded therein, the non-crosslinked hyaluronic acid dissolving at a fast rate to release calcein (fast-release). In addition, the fluorescent signal of calcein was strongly observed even 120 minutes after skin penetration, and thus the microstructure of the present invention can release calcein slowly and continuously after skin penetration. This extended-release effect is thought to be due to the crosslinked hyaluronic acid with calcein loaded therein, the crosslinked hyaluronic acid slowly dissolving to release calcein, and such an effect was expected to be maintained for 4-6 hours in light of the results of the present example and example 2 above. Therefore, the microstructure of the present invention can be effectively used as a drug delivery vehicle in a form of loading a drug and releasing the drug into the skin, and can easily control the release rate of drugs, such as increasing the amount of a drug released in an extended-release manner by increasing the mixing proportion of crosslinked hyaluronic acid in the manufactured microstructure, and increasing the amount of a drug released in a fast-release manner by increasing the mixing proportion of non-crosslinked hyaluronic acid.

Example 6: Experiment of Dissolution Pattern and Dissolution Rate Over Time when Present Microstructure Manufactured of Fluorescent Substance-Conjugated Hyaluronic Acid (Fluorescein Hyaluronic Acid) Penetrates Skin In order to investigate the dissolution pattern and dissolution rate of the microstructure of the present invention in the skin when the microstructure penetrates the skin, the dissolution pattern and dissolution rate of the microstructure of the present invention manufactured of a fluorescent substance-conjugated hyaluronic acid were checked when the microstructure penetrated the porcine skin.

As a biocompatible polymer, hyaluronic acid having an average molecular weight of 360 kDa (molecular weight range of 240-490 kDa) was used. Here, fluorescent substance-conjugated hyaluronic acid (fluorescein-tagged hyaluronic acid) was prepared by adding fluorescent substance-conjugated hyaluronic acid (fluorescein-labeled hyaluronic acid, average molecular weight: 800 kDa, Sigma Aldrich) at a proportion of 5% (w/w) and using BDDE as a crosslinking agent. Then, hyaluronic acid was added to purified water such that the crosslinked hyaluronic acid was contained at a mixing proportion of 30% (w/w) relative to the weight of the overall hyaluronic acid (non-crosslinked hyaluronic acid and crosslinked hyaluronic acid), followed by complete dissolution, to prepare a crosslinked hyaluronic acid hydrogel polymer. The polymer was supplied, injected, and dried in a PDMS micromold, followed by demolding, to manufacture a microstructure (microneedle) with a height of 265 μm.

The microstructure sample was cut into 0.7 cm×0.7 cm before use, and then allowed to penetrate the porcine skin by a vertical application of a force of 5 kgf for 1 minute, 30 minutes, and 120 minutes. The fluorescent substance remaining on the porcine skin was observed using a confocal microscope (Nikon, ECLIPSE TE2000-E) to check the penetration depth, dissolution pattern, and dissolution rate.

Figure 8A:
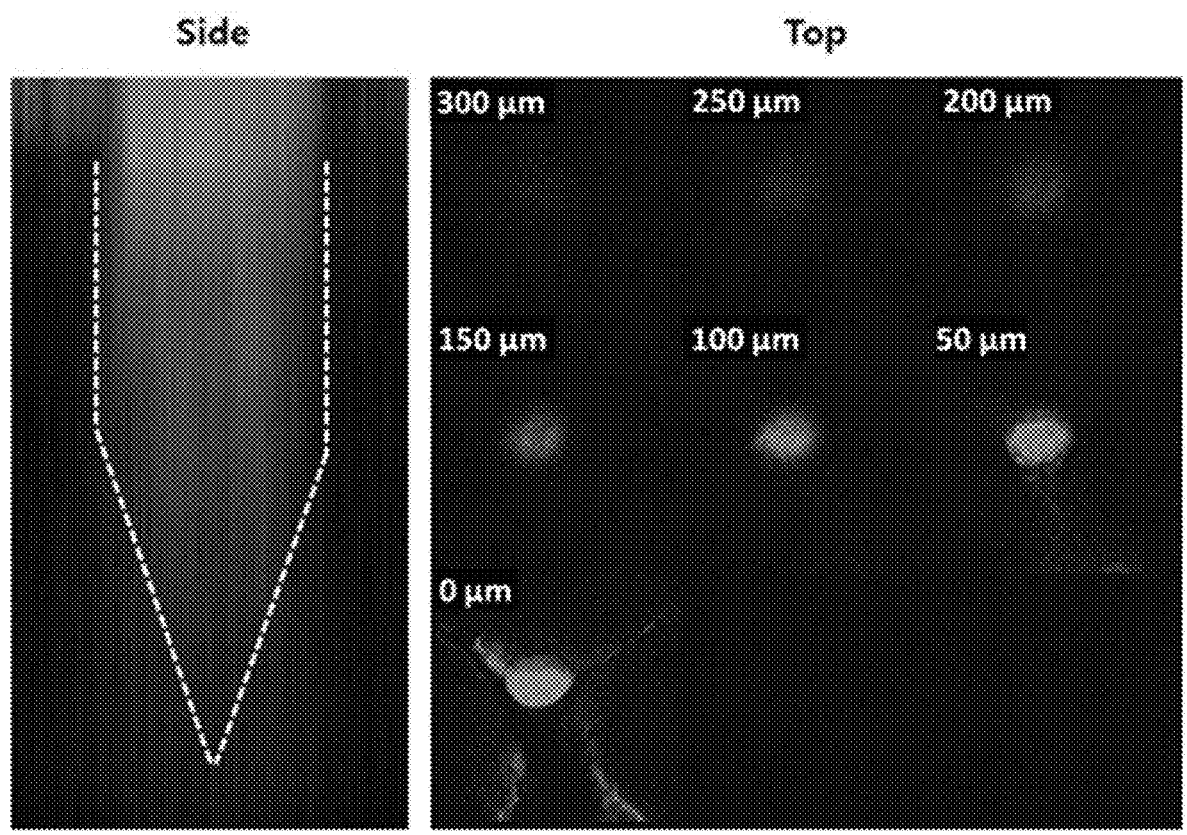
FIGS. 8a, 8b and 8c show the diffusion pattern of a fluorescent substance (fluorescein) according to the penetration time (1 minute, 30 minutes, and 120 minutes) after a microstructure of the present invention with the fluorescent substance conjugated thereto was allowed to penetrate the porcine skin.
Figure 8B:
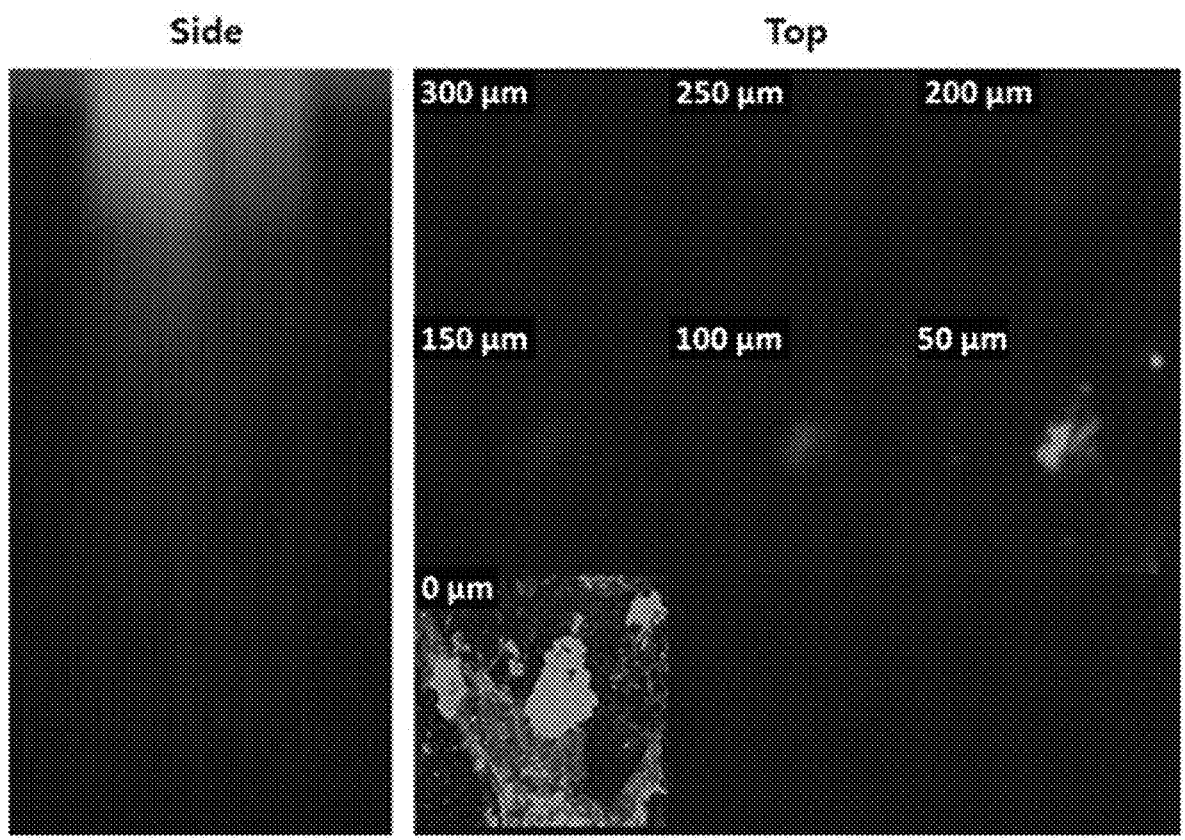
Figure 8C:
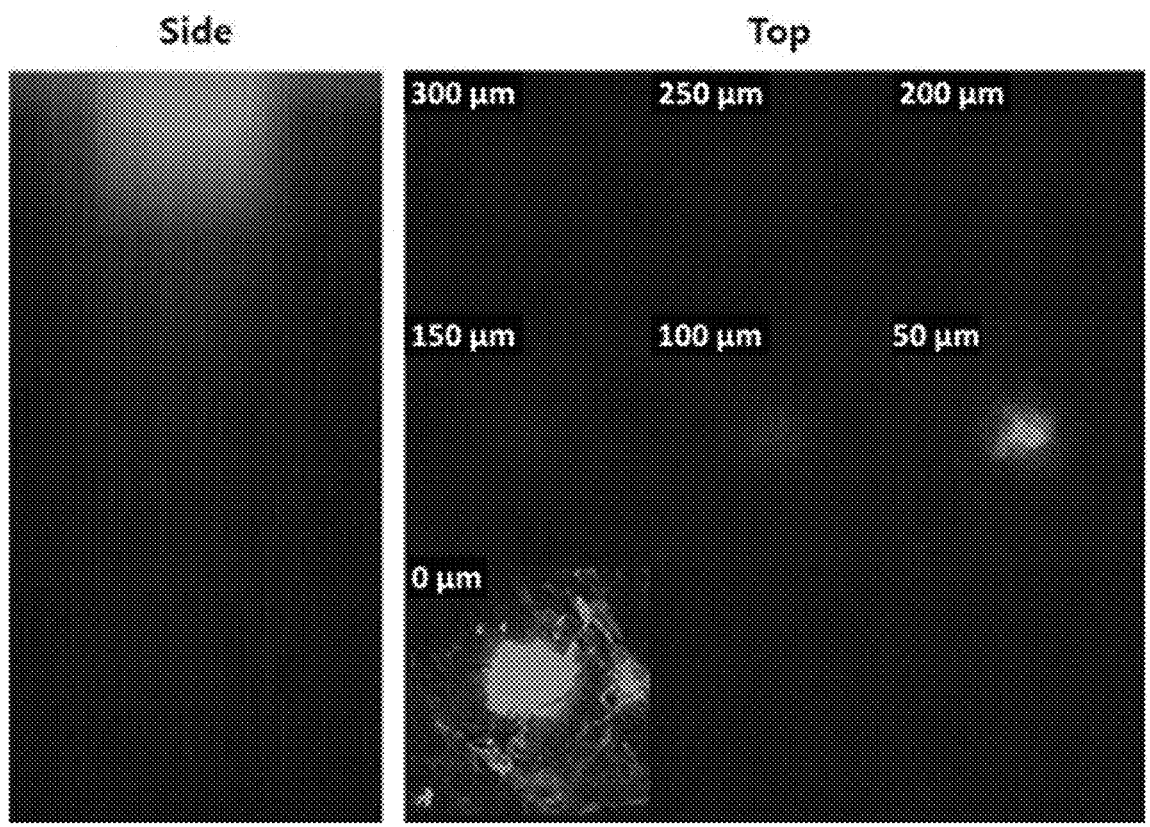

The results are shown in FIGS. 8a to 8c.

As shown in FIGS. 8a to 8c, skin penetration was made to 80% or more of the total needle length (265 μm) 1 minute after skin penetration, and a tip portion of the needle started to dissolve. The fluorescent substance-conjugated crosslinked hyaluronic acid dissolved and diffused at a very slow rate from 30 minutes to 120 minutes after the penetration, unlike non-crosslinked hyaluronic acid dissolving very fast immediately after the skin penetration, and the fluorescent signal was maintained for 120 minutes or longer while the shape of the microneedle was maintained, and the fluorescent signal was expected to be maintained for 4-6 hours in light of the present example and example 2 above. Therefore, the microstructure of the present invention has excellent dissolution characteristics at the time of skin penetration, and the dissolution rate of the microstructure can be easily controlled by increasing or decreasing the mixing proportion of crosslinked hyaluronic acid to dissolve the microstructure slowly for a long time or fast for a short time.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A skin penetrating microneedle comprising, as a main ingredient, i) crosslinked hyaluronic acid or ii) a mixture of crosslinked hyaluronic acid and non-crosslinked hyaluronic acid, wherein, relative to the weight of the overall hyaluronic acid, the content of the crosslinked hyaluronic acid is 5-100% (w/w) and the content of the non-crosslinked hyaluronic acid is 0-95% (w/w),
wherein the skin penetrating microneedle has a length of 80-1500 μm,
wherein a tip of the skin penetrating microneedle is in a cone shape, and configured to penetrate the skin,
wherein when the microneedle is allowed to penetrate the skin by a force of 3 kgf, the microneedle shows a dissolution rate at which, on the basis of the length of the microneedle, 60% or less dissolves 10 minutes after skin penetration, 75% or less dissolves 30 minutes after skin penetration, and 85% or less dissolves 60 minutes after skin penetration.

2. The skin penetrating microneedle of claim 1, wherein the crosslinked hyaluronic acid is 15-30% on the basis of the weight of the overall hyaluronic acid when the microneedle is allowed to penetrate the skin by a force of 3 kgf, the microneedle shows a dissolution rate at which, on the basis of the length of the microneedle, 50-60% dissolves 10 minutes after skin penetration, 65-75% dissolves 30 minutes after skin penetration, and 70-85% dissolves 60 minutes after skin penetration.

3. The skin penetrating microneedle of claim 1, wherein the crosslinked hyaluronic acid is 30-35% on the basis of the weight of the overall hyaluronic acid when the microneedle is allowed to penetrate the skin by a force of 3 kgf, the microneedle shows a dissolution rate at which, on the basis of the length of the microneedle, 45-55% dissolves 10 minutes after skin penetration, 56-68% dissolves 30 minutes after skin penetration, and 65-75% dissolves 60 minutes after skin penetration.

4. The skin penetrating microneedle of claim 1, wherein the crosslinked hyaluronic acid is 35-50% on the basis of the weight of the overall hyaluronic acid when the microneedle is allowed to penetrate the skin by a force of 3 kgf, the microneedle shows a dissolution rate at which, on the basis of the length of the microneedle, 40-55% dissolves 10 minutes after skin penetration, 51-61% dissolves 30 minutes after skin penetration, and 55-65% dissolves 60 minutes after skin penetration.

5. The skin penetrating microneedle of claim 1, wherein the crosslinked hyaluronic acid is 50-70% on the basis of the weight of the overall hyaluronic acid when the microneedle is allowed to penetrate the skin by a force of 3 kgf, the microneedle shows a dissolution rate at which, on the basis of the length of the microneedle, 35-45% dissolves 10 minutes after skin penetration, 44-54% dissolves 30 minutes after skin penetration, and 48-58% dissolves 60 minutes after skin penetration.

6. The skin penetrating microneedle of claim 1, wherein the crosslinked hyaluronic acid is 70-90% on the basis of the weight of the overall hyaluronic acid when the microneedle is allowed to penetrate the skin by a force of 3 kgf, the microneedle shows a dissolution rate at which, on the basis of the length of the microneedle, 35-45% dissolves 10 minutes after skin penetration, 41-51% dissolves 30 minutes after skin penetration, and 45-56% dissolves 60 minutes after skin penetration.

7. The skin penetrating microneedle of claim 1, wherein the concentration of the hyaluronic acid is 1-10% (w/v) relative to water or an aqueous solvent constituting i) the crosslinked hyaluronic acid or ii) the hyaluronic acid mixture.

8. The skin penetrating microneedle of claim 1, wherein the molecular weight of the crosslinked and the non-crosslinked hyaluronic acid is 100-5000 kDa.

9. The skin penetrating microneedle of claim 1, wherein the crosslinked hyaluronic acid has a degree of crosslinking of 1-50%.

10. The skin penetrating microneedle of claim 1, wherein the microneedle has a Young's modulus of 0.4-0.7 N/100 µm.

11. The skin penetrating microneedle of claim 1, wherein 80% of the microneedle penetrates the skin.

12. The skin penetrating microneedle of claim 1, wherein the microneedle further comprises a biocompatible polymer or an adhesive.

13. The skin penetrating microneedle of claim 12, wherein the biocompatible polymer is at least one polymer selected from the group consisting of carboxymethyl cellulose (CMC), alginic acid, pectin, carrageenan, chondroitin (sulfate), dextran (sulfate), chitosan, polylysine, collagen, gelatin, carboxymethyl chitin, fibrin, agarose, pullulan polylactide, polyglycolide (PGA), polylactide-glycolide copolymer (PLGA), pullulan polyanhydride, polyorthoester, polyetherester, polycaprolactones, polyesteramide, poly(butyric acid), poly(valeric acid), polyurethane, polyacrylate, ethylene-vinyl acetate polymer, acrylic substituted cellulose acetate, non-degradable polyurethane, polystyrene, polyvinyl chloride, polyvinyl fluoride, poly(vinyl imidazole), chlorosulphonate polyolefin, polyethylene oxide, polyvinylpyrrolidone (PVP), polyethylene glycol (PEG), polymethacrylate, hydroxypropyl methylcellulose (HPMC), ethylcellulose (EC), hydroxypropyl cellulose (HPC), cyclodextrin, copolymers of monomers forming these polymers, and cellulose.

14. The skin penetrating microneedle of claim 12, wherein the adhesive is at least one adhesive selected from the group consisting of silicone, polyurethane, a physical adhesive (Gecko), polyacryl, ethyl cellulose, hydroxy methyl cellulose, ethylene vinyl acetate, and polyisobutylene.

15. The skin penetrating microneedle of claim 1, wherein the microneedle further comprises a pharmacologically active ingredient or a cosmetical ingredient.

* * * * *